United States Patent [19]
Weigl et al.

[11] Patent Number: 5,972,710
[45] Date of Patent: *Oct. 26, 1999

[54] MICROFABRICATED DIFFUSION-BASED CHEMICAL SENSOR

[75] Inventors: Bernhard H. Weigl; Paul Yager; James P. Brody; Mark R. Holl, all of Seattle; Margaret Kenny, Edmonds; David Schutte, Auburn; Gregory Hixson, Seattle; M. Diane Zebert, Seattle; Andrew Kamholz, Seattle; Caicai Wu, Seattle; Eric Altendorf, Seattle, all of Wash.

[73] Assignee: University of Washington, Seattle, Wash.

[*] Notice: This patent is subject to a terminal disclaimer.

[21] Appl. No.: 08/829,679

[22] Filed: Mar. 31, 1997

Related U.S. Application Data

[63] Continuation-in-part of application No. 08/625,808, Mar. 29, 1996, Pat. No. 5,716,852.

[51] Int. Cl.⁶ .................................................. G01N 21/64
[52] U.S. Cl. ........................... 436/34; 436/172; 436/177; 436/180; 422/81
[58] Field of Search ..................... 436/172, 177, 436/180, 52, 34; 422/81, 82, 82.08; 356/246, 440

[56] References Cited

U.S. PATENT DOCUMENTS

| | | | |
|---|---|---|---|
| 3,449,938 | 6/1969 | Giddings | 73/23 |
| 3,795,489 | 3/1974 | Warnick et al. | 23/254 R |
| 4,147,621 | 4/1979 | Giddings | 210/22 C |
| 4,214,981 | 7/1980 | Giddings | 209/155 |
| 4,250,026 | 2/1981 | Giddings et al. | 209/155 |
| 4,683,212 | 7/1987 | Uffenheimer | 436/52 |
| 4,726,929 | 2/1988 | Gropper et al. | 422/68 |
| 4,737,268 | 4/1988 | Giddings | 209/12 |
| 4,756,884 | 7/1988 | Hillman et al. | 422/73 |
| 4,830,756 | 5/1989 | Giddings | 210/739 |

(List continued on next page.)

FOREIGN PATENT DOCUMENTS

| | | |
|---|---|---|
| 0 249 701 B1 | 12/1988 | European Pat. Off. |
| 0 381 501 A2 | 8/1990 | European Pat. Off. |
| 0 645 169 A1 | 3/1995 | European Pat. Off. |
| WO 93/22053 | 11/1993 | WIPO |
| WO 96/04547 | 2/1996 | WIPO |
| WO 96/12541 | 5/1996 | WIPO |
| WO 96/15576 | 5/1996 | WIPO |
| WO 97/00125 | 1/1997 | WIPO |
| WO 97/02357 | 1/1997 | WIPO |

OTHER PUBLICATIONS

Chmelik, Josef, "Isoelectric focusing field–flow fractionation" *Journal of Chromatography* 545, No. 2 (1991).

Brody, J.P. and Yager, P. (1996), "Low Reynolds Number Micro–Fluidic Devices," Solid State Sensor & Actuator Workshop, Hilton Head, SC, Jun. 2–6, 1996, pp. 105–108.

(List continued on next page.)

*Primary Examiner*—Jeffrey Snay
*Attorney, Agent, or Firm*—Greenlee, Winner and Sullivan, P.C.

[57] ABSTRACT

A channel-cell system is provided for detecting the presence and/or measuring the presence of analyte particles in a sample stream comprising: a) a laminar flow channel; b) two inlets in fluid connection with the laminar flow channel for respectively conducting into the laminar flow channel (1) an indicator stream which may comprise an indicator substance which indicates the presence of the analyte particles by a detectable change in property when contacted with the analyte particles, and (2) the sample stream; c) wherein the laminar flow channel has a depth sufficiently small to allow laminar flow of the streams and a length sufficient to allow particles of the analyte to diffuse into the indicator stream to the substantial exclusion of the larger particles in the sample stream to form a detection area; and d) an outlet for conducting the streams out of the laminar flow channel to form a single mixed stream.

19 Claims, 10 Drawing Sheets

U.S. PATENT DOCUMENTS

| | | | |
|---|---|---|---|
| 4,894,146 | 1/1990 | Giddings | 209/12 |
| 4,908,112 | 3/1990 | Pace | 204/299 |
| 5,039,426 | 8/1991 | Giddings | 210/695 |
| 5,141,651 | 8/1992 | Giddings | 210/748 |
| 5,156,039 | 10/1992 | Giddings | 79/1 R |
| 5,193,688 | 3/1993 | Giddings | 209/155 |
| 5,240,618 | 8/1993 | Caldwell et al. | 210/748 |
| 5,250,263 | 10/1993 | Manz | 422/81 |
| 5,288,463 | 2/1994 | Chemelli | 422/58 |
| 5,304,487 | 4/1994 | Wilding et al. | 435/291 |
| 5,389,524 | 2/1995 | Larsen et al. | 435/29 |
| 5,465,849 | 11/1995 | Wada et al. | 209/214 |
| 5,480,614 | 1/1996 | Kamahori | 422/70 |
| 5,599,432 | 2/1997 | Manz et al. | 204/451 |
| 5,599,503 | 2/1997 | Manz et al. | 422/82.05 |
| 5,635,358 | 6/1997 | Wilding et al. | 435/7.2 |
| 5,637,469 | 6/1997 | Wilding et al. | 435/7.21 |
| 5,716,852 | 2/1998 | Yager et al. | 436/172 |
| 5,726,751 | 3/1998 | Altendorf et al. | 356/246 |

OTHER PUBLICATIONS

Faucheux, L.P. et al. (1995), "Optical Thermal Ratchet," Phys. Rev. Lett. 74:1504–1507.

Giddings, J.C. (1985), "Optimized Field–Flow Fractionation System Based on Dual Stream Splitters," Anal. Chem. 57:945–947.

Giddings, J.C. et al. (1983), "Outlet Stream Splitting for Sample Concentration in Field–Flow Fractionation," Separation Science and Technology 18:293–306.

Giddings, J.C. (1993), "Field–Flow Franctionation: Analysis of Macromolecular, Colloidal and Particulate Materials," Science 260:1456–1465.

Leff, H.S. and Rex, A.F. (1990), "Resource letter MD–1: Maxwell's demon," Am. J. Phys. 58:201–209.

Petersen, K.E. (1982), "Silicon as a Mechanical Material," Proc. IEEE 70(5):420–457.

Reisman, A. et al. (1979), "The Controlled Etching of Silicon in Catalyzed Ethylenediamine–Pyrocatechol–Water Solutions," J. Electrochem. Soc. 126:1406–1415.

Rousselet, J. et al. (1994), "Directional motion of brownian particles induced by a periodic asymmetric potential," Nature 370:446–448.

Shoji, S. and Esashi, M. (1994), "Microflow devices and systems," J. Micromech. and Microeng. 4:157–171.

Wallis, G. and Pomerantz, D.I. (1969), "Field Assisted Glass–Metal Sealing," J. Appl. Phys. 40:3946–3949.

Weigl, B.H. and Yager, P. (1996), "Silicon–Microfabricated Diffusion–Based Optical Chemical Sensor," presented at Europtrode Conference, Zurich, Switzerland, Apr. 2–3, 1996.

Weigl, B.H. et al. (1997), "Fluorescence and absorbance analyte sensing in whole blood and plasma based on diffusion separation in silicon–microfabricated flow structures," SPIE Proceedings, J. Lakowitz (ed.), Fluorescence Sensing Technology III (Feb. 9–11, 1997).

Weigl, B. H. et al. (1996), "Diffusion–Based Opitcal Chemical Detection in Silicon Flow Structures," Analytical Methods & Instrumentation Special Issue $\mu$TAS 96, pp. 174–184.

Weigl, B.H. et al. (1996), "Rapid sequential chemical analysis in microfabricated flow structures using multiple fluorescent reporter beads," $\mu$TAS 96 (Nov '96).

Williams, P.S. et al. (1992), "Continuous SPLITT Fractionation Based on a Diffusion Mechanism," Ind. Eng. Chem. Res. 31:2172–2181.

Manz, A. et al., "Planar Chips Technology for Miniaturization of Separation Systems: A Developing Perspective in Chemical Monitoring, " (1993) *Advances in Chromatography* 33:2–66.

Verpoorte, E.M.J. et al., "Three–dimensional micro flow manifolds for miniaturized chemical analysis systems," (1994) *J. Micromech. Microeng.* 4:246–256.

MICROFABRICATED DIFFUSION-BASED CHEMICAL SENSOR

This application is a continuation-in-part of Ser. No. 625,808, filed Mar. 29, 1996, now U.S. Pat. No. 5,716,852.

This invention was made with government support under Army research contract DAMD17-94-J-4460 awarded by the U.S. Army. The government has certain rights in the invention.

FIELD OF THE INVENTION

This invention relates generally to microsensors and methods for analyzing the presence and concentration of small particles in streams containing both these small particles and larger particles by diffusion principles. The invention is useful, for example, for analyzing blood to detect the presence of small particles such as hydrogen, sodium or calcium ions in a stream containing cells.

BACKGROUND OF THE INVENTION

In Maxwell's famous gedanken (thought) experiment, a demon operates a door between two boxes of gas at the same temperature. The demon sorts the molecules keeping the faster molecules in one box and the slower in the other, violating the basic laws of thermodynamics. This paradox has since been resolved in many different ways. Leff, H. S. and Rex, A. F. (1990), "Resource letter md-1: Maxwell's demon," Am. J. Physics 58:201–209.

A similar arrangement can be used to separate particles. Consider a mixture of particles of two different sizes suspended in water in one box and pure water in the other. If the demon opens and closes the door between the boxes quickly enough so that none of the larger particles have time to diffuse through the doorway, but long enough so that some of the smaller particles have enough time to diffuse into the other box, some separation will be achieved.

Recently two experiments have been done where a spatially asymmetric potential is periodically applied in the presence of a number of brownian particles. Faucheux, L. S., et al. (1995), "Optical thermal ratchet," Physical Rev. Letters 74:1504–1507; Rousselet, J., et al. (1994), "Directional motion of brownian particles induced by a periodic asymmetric potential," Nature 370:446–448.

This has been shown to lead to a directed motion of the particles at a rate depending on the diffusion coefficient. One experiment (Rousselet, J., et al. (1994), "Directional motion of brownian particles induced by a periodic asymmetric potential," Nature 370:446–448) used microfabricated electrodes on a microscope slide to apply an electric field for the potential. This idea is also the subject of European Patent Publication 645169 of Mar. 29, 1995, for "Separation of particles in a fluid using a saw-tooth electrode and an intermittent excitation field," Adjari, A., et al. The other experiment (Faucheux, L. S., et al. (1995), "Optical thermal ratchet," Physical Rev. Letters 74:1504–1507) used a modulated optical tweezer arrangement.

Diffusion is a process which can easily be neglected at large scales, but rapidly becomes important at the microscale. The average time t for a molecule to diffuse across a distance d is $t=d^2/D$ where D is the diffusion coefficient of the molecule. For a protein or other large molecule, diffusion is relatively slow at the macro-scale (e.g. hemoglobin with D equal to $7\times10^{-7}$ $cm^2/s$ in water at room temperature takes about 106 seconds (ten days) to diffuse across a one centimeter pipe, but about one second to diffuse across a ten micron channel).

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests.

A process called "field-flow fractionation" (FFF) has been used to separate and analyze components of a single input stream in a system not made on the microscale, but having channels small enough to produce laminar flow. Various fields, including concentration gradients, are used to produce a force perpendicular to the direction of flow to cause separation of particles in the input stream. See, e.g. Giddings, J. C., U.S. Pat. No. 3,449,938, Jun. 17, 1969, "Method for Separating and Detecting Fluid Materials;" Giddings, J. C., U.S. Pat. No. 4,147,621, Apr. 3, 1979, "Method and Apparatus for Flow Field-Flow Fractionation;" Giddings, J. C., U.S. Pat. No. 4,214,981, Jul. 29, 1980), "Steric Field-Flow Fractionation;" Giddings, J. C., et al., U.S. Pat. No. 4,250,026, Feb. 10, 1981, "Continuous Steric FFF Device for The Size Separation of Particles;" Giddings, J. C., et al., (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation;" Giddings, J. C., U.S. Pat. No. 4,141,651, Aug. 25, 1992, "Pinched Channel Inlet System for Reduced Relaxation Effects and Stopless Flow Injection in Field-Flow Fractionation;" Giddings, J. C., U.S. Pat. No. 5,156,039 Oct. 20, 1992, "Procedure for Determining the Size and Size Distribution of Particles Using Sedimentation Field-Flow Fractionation;" Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements;" Caldwell, K. D. et al., U.S. Pat. No. 5,240,618, Aug. 31, 1993, "Electrical Field-Flow Fractionation Using Redox Couple Added to Carrier Fluid;" Giddings, J. C. (1993), "Field-Flow Fractionation: Analysis of Macromolecular, Colloidal and Particulate Materials," Science 260:1456–1465; Wada, Y., et al., U.S. Pat. No. 5,465,849, Nov. 14, 1995, "Column and Method for Separating Particles in Accordance with their Magnetic Susceptibility." None of these references disclose the use of a separate input stream to receive particles diffused from a particle-containing input stream.

A related method for particle fractionation is the "Split Flow Thin Cell" (SPLITT) process. See, e.g., Williams, P. S., et al. (1992), "Continuous SPLITT Fractionation Based on a Diffusion Mechanism," Ind. Eng. Chem. Res. 31:2172–2181; and J. C. Giddings U.S. Pat. No. 5,039,426. These publications disclose channel cells with channels small enough to produce laminar flow, but again only provide for one inlet stream. A further U.S. patent to J. C. Giddings, U.S. Pat. No. 4,737,268, discloses a SPLITT flow cell having two inlet streams (FIG. 3); however the second inlet stream is not an indicator stream, but rather a particle-free stream. Giddings U.S. Pat. No. 4,894,146 also discloses a SPLITT flow cell having two input streams, but no indicator stream. All these SPLITT flow methods require the presence of more than one output stream for separating various particle fractions.

None of the foregoing publications describe a channel system capable of analyzing small particles in very small quantities of sample containing larger particles, particularly larger particles capable of affecting the indicator used for the analysis. No devices or methods using indicator streams within the cell system are described.

SUMMARY OF THE INVENTION

Microfluidic devices allow one to take advantage of diffusion as a rapid separation mechanism. Flow behavior in microstructures differs significantly from that in the macroscopic world. Due to extremely small inertial forces in such structures, practically all flow in microstructures is laminar. This allows the movement of different layers of fluid and particles next to each other in a channel without any mixing other than diffusion. On the other hand, due to the small lateral distances in such channels, diffusion is a powerful tool to separate molecules and small particles according to their diffusion coefficients, which is usually a function of their size.

This invention provides a channel cell system for detecting the presence of analyte particles in a sample stream also comprising larger particles comprising:

a) a laminar flow channel;
b) at least two inlet means in fluid connection with said laminar flow channel for respectively conducting into said laminar flow channel (1) indicator stream, said indicator stream preferably comprising an indicator substance, for example, a pH-sensitive dye, which indicates the presence of said analyte particles by a detectable change in property when contacted with said analyte particles, and (2) said sample stream;
c) wherein said laminar flow channel has a depth sufficiently small to allow laminar flow of said streams adjacent to each other and a length sufficient to allow analyte particles to diffuse into said indicator stream to the substantial exclusion of said larger particles in said sample stream to form a detection area;
d) outlet means for conducting said streams out of said laminar flow channel to form a single mixed stream.

In the simplest embodiment of this invention, a single indicator stream and a single sample stream are used; however, the methods and devices of this invention may also use multiple sample and/or indicator streams, and reference or calibration streams, all in laminar flow with each other.

The preferred embodiments of this invention utilize liquid streams, although the methods and devices are also suitable for use with gaseous streams. The term "fluid connection" means that fluid flows between the two or more elements which are in fluid connection with each other.

The term "detection" as used herein means determination that a particular substance is present. Typically, the concentration of a particular substance is determined. The methods and apparatuses of this invention can be used to determine the concentration of a substance in a sample stream.

The channel cell system of this invention may comprise external detecting means for detecting changes in an indicator substance carried within the indicator stream as a result of contact with analyte particles. Detection and analysis is done by any means known to the art, including optical means, such as optical spectroscopy, and other means such as absorption spectroscopy or fluorescence, by chemical indicators which change color or other properties when exposed to the analyte, by immunological means, electrical means, e.g. electrodes inserted into the device, electrochemical means, radioactive means, or virtually any microanalytical technique known to the art including magnetic resonance techniques, or other means known to the art to detect the presence of an analyte such as an ion, molecule, polymer, virus, DNA sequence, antigen, microorganism or other factor. Preferably optical or fluorescent means are used, and antibodies, DNA sequences and the like are attached to fluorescent markers.

The term "particles" refers to any particulate material including molecules, cells, suspended and dissolved particles, ions and atoms.

The input stream may be any stream containing particles of the same or different size, for example blood or other body fluid, contaminated drinking water, contaminated organic solvents, urine, biotechnological process samples, e.g. fermentation broths, and the like. The analyte may be any smaller particle in the input stream which is capable of diffusing into the indicator stream in the device, e.g. hydrogen, calcium or sodium ions, proteins, e.g. albumin, organic molecules, drugs, pesticides, and other particles. In the preferred embodiment when the sample stream is whole blood, small ions such as hydrogen and sodium diffuse rapidly across the channel, whereas larger particles such as those of large proteins, blood cells, etc. diffuse slowly. Preferably the analyte particles are no larger than about 3 micrometers, more preferably no larger than about 0.5 micrometers, or are no larger than about 1,000,000 MW, and more preferably no larger than about 50,000 MW.

The system may also include an indicator stream introduced into one of the inlet means comprising a liquid carrier containing substrate particles such as polymers or beads having an indicator substance immobilized thereon. The system may also include an analyte stream comprising substrate particles such as polymer beads, antibodies and the like on which an indicator substance is immobilized. The liquid carrier can be any fluid capable of accepting particles diffusing from the feed stream and containing an indicator substance. Preferred indicator streams comprise water and isotonic solutions such as salt water with a salt concentration of about 10 mM NaCl, KCl or MgCl, or organic solvents like acetone, isopropyl alcohol, ethanol, or any other liquid convenient which does not interfere with the effect of the analyte on the indicator substance or detection means.

The channel cell may be fabricated by microfabrication methods known to the art, e.g. as exemplified herein, a method comprising forming channels in a silicon microchip, such as by etching grooves into the surface of the silicon microchip and placing a glass cover over the surface. Precision injection molded plastics may also be used for fabrication.

The method of this invention is designed to be carried out such that all flow is laminar. In general, this is achieved in a device comprising microchannels of a size such that the Reynolds number for flow within the channel is below about 1, preferably below about 0.1. Reynolds number is the ratio of inertia to viscosity. Low Reynolds number means that inertia is essentially negligible, turbulence is essentially negligible, and, the flow of the two adjacent streams is laminar, i.e. the streams do not mix except for the diffusion of particles as described above. Flow can be laminar with Reynolds number greater than 1. However, such systems are prone to developing turbulence when the flow pattern is disturbed, e.g., when the flow speed of a stream is changed, or when the viscosity of a stream is changed.

The laminar flow channel is long enough to permit small analyte particles to diffuse from the sample stream and have a detectable effect on an indicator substance or detection means, preferably at least about 2 mm long. The length of the flow channel depends on its geometry. The flow channel can be straight or curved in any of a number of ways. In one embodiment, the flow channel can include one or more "hairpin turns," making a tight stairstep geometry. In another embodiment, the flow channel can be in the shape of a coil, like a neatly wound up garden hose. Non-straight channel geometries allow for increasing the length of the flow channel without increasing the size/diameter of the substrate plate in which the channel is formed, e.g., a silicon microchip. The diffusion coefficient of the analyte, which is usually inversely proportional to the size of the analyte, affects the desired flow channel length. For a given flow speed, particles with smaller diffusion coefficients require a longer flow channel to have time to diffuse into the indicator stream.

Alternatively, to allow more time for diffusion to occur, the flow rate can be decreased. However, several factors limit the minimum flow rate and therefore make a longer flow channel desirable in some cases. First, the flow rate is achieved by a pumping means or pressure source, some of which cannot produce as low a pressure and flow rate as may be desired, to allow enough time for diffusion of particles with small diffusion coefficients. Second, if the flow rate is slow enough and some particles are of significantly different density from the surrounding fluid streams, particles denser than the surrounding fluid streams may sink to the bottom of the flow channel and particles less dense than the surrounding fluid streams may float to the top of the flow channel. It is preferable that the flow rate be fast enough that hydrodynamic forces substantially prevent particles from sticking to the bottom, top, or walls of the flow channel. Third, a small change in pressure leads to larger errors in measurement accuracy at lower flow rates. Fourth, at low flow rates, other factors, such as changes in viscosity of fluids, can lead to larger errors in measurement accuracy.

The flow channel can be straight or non-straight, i.e., convoluted. A convoluted flow channel as used herein refers to a flow channel which is not straight. A convoluted channel can be, for example, coiled in a spiral shape or comprise one or a plurality of "hairpin" curves, yielding a square wave shape. Convoluted channels provide longer distances for diffusion to occur, thereby allowing for measurement of analytes with larger diffusion coefficients, e.g., typically larger analytes. In preferred embodiments of this invention wherein a silicon microchip is the substrate plate in which the flow channel is formed, the channel length of a straight flow channel is between about 5 mm and about 50 mm. In preferred embodiments of this invention wherein the flow channel is convoluted, i.e., non-straight, the length of the flow channel is defined or limited only by the size of the microchip or other substrate plate into which the channel is etched or otherwise formed. The channel width (diffusion direction) is preferably between about 20 micrometers and about 1 mm. The channel is more preferably made relatively wide, e.g. at least about 200 micrometers, which makes it easier to measure indicator fluorescence with simple optics, and less likely for particles to clog the channel. However, the channel can be made as narrow as possible while avoiding clogging the channel with the particles being used. Narrowing the width of the channel makes diffusion occur more rapidly, and thus detection can be done more rapidly. The channel depth is small enough to allow laminar flow of two streams therein, preferably no greater than about 1000 micrometers and more preferably between about 50 micrometers and about 400 micrometers.

In some embodiments, the laminar flow channel may be long enough to allow the indicator and sample streams to reach equilibrium with respect to the analyte particles within the channel. Equilibrium occurs when the maximum amount of smaller particles have diffused into the indicator stream.

The system may also comprise specimen channel and outlet means such as smaller channels for conducting specimen streams from the indicator stream at successive intervals along the length of the laminar flow channel, and means including viewports and fluorescence detectors for measuring changes in an indicator substance in each specimen stream, whereby concentration of the analyte in the sample stream may be determined.

Dual detection embodiments of the device of the present invention which allow for detection of both undissolved and dissolved analytes are also provided. Detection of both undissolved and dissolved analytes can be achieved in one dual detection device: dissolved particles can be detected in the flow channel of the T-sensor and undissolved particles can be detected in a v-groove channel or sheath flow module, either or both of which can be in fluid connection with a T-sensor flow channel. Branching flow channels can provide for fluid connection between a T-sensor flow channel and a v-groove channel and/or sheath flow module.

The channel cell systems of this invention can be in fluid connection with a v-groove flow channel, which preferably has a width at the top small enough to force the particles into single file but large enough to pass the largest particles without clogging. V-groove channels are formed by anisotropic EPW (ethylenediamine-pyrocatechol-water) etching of single crystalline silicon microchips, providing access to reflective surfaces with precisely etched angles relative to the surface of the microchip (Petersen, Proc. IEEE 70 (5): 420–457, 1982). (U.S. patent application Ser. No. 08/534,515, "Silicon Microchannel Optical Flow Cytometer," filed Sep. 27, 1995, now U.S. Pat. No. 5,726,751, which is incorporated by reference herein in its entirety, discloses a flow cytometer comprising a v-groove flow channel formed by micromachining a silicon microchip.) The cross-section of such a channel is like a letter V, and thus is referred to as a v-groove channel. An optical head comprising a laser and small and large angle photodetectors adapted for use with a v-groove flow channel can be employed as well. As described in U.S. patent application Ser. No. 08/534,515, now U.S. Pat. No. 5,726,751, detectors placed at small and large angles with respect to the portion of the probe beam reflected from the v-groove wall can be used to count particles, such as cells, and distinguish them by size (via small angle detector) and structure/morphology (via large angle detector). Using an appropriate laser or LED source, e.g., a blue laser, which can be determined by routine choice by those of ordinary skill in the art, fluorescence detection can be performed by placing an appropriate filter in front of the large angle detector.

The flow channel of the T-sensor can be in fluid connection with a v-groove channel allowing for dual detection of dissolved and undissolved, single-file particles with one device. The fluid streams can flow first through a T-sensor flow channel and then through a v-groove channel, via branching flow channels. Alternatively, the fluid stream can flow first through a v-groove channel and then through a T-sensor flow channel.

An alternative means of achieving single file particle flow through a flow channel is the sheath flow module disclosed in U.S. patent application Ser. No. 08/823,747 "Device and Method for 3-Dimensional Alignment of Particles in Microfabricated Flow Channels," filed Mar. 26, 1997 and specifically incorporated in its entirety by reference herein. The sheath flow module includes a first plate of material having formed therein a laminar fluid flow channel; at least two inlets, each inlet joining the laminar flow channel at a junction, the first inlet junction being wider than the second inlet junction, and an outlet from the flow channel. A second plate, e.g., a transparent cover plate, seals the module and allows for optical measurements. A transparent cover plate allows for optical measurements by reflection, in cases where the first plate is a reflective material, e.g., silicon. A first inlet allows for introduction of a first fluid into the flow channel. The first fluid is the sheath fluid. A second inlet allows for introduction of a second fluid into the sheath fluid while it is flowing through the flow channel. The second fluid is the center fluid. Because the second inlet junction is narrower than the first inlet junction, the center fluid becomes surrounded on both sides by the sheath fluid. After all fluids have been introduced and sheath flow has been achieved, the depth of the flow channel can be decreased, leading to vertical hydrodynamic focusing. Optionally, the width of the flow channel can be decreased, leading to horizontal hydrodynamic focusing. The decrease in depth and width can be gradual or abrupt. Hydrodynamic focusing in the sheath flow module leads to single file particle flow.

The sheath flow module can be in fluid connection with the channel cell system of the present invention. The fluid streams can flow first through a T-sensor flow channel and then through a sheath flow module. Alternatively, the fluid stream can flow first through a sheath flow module and then through a T-sensor flow channel.

The channel cell system of a preferred embodiment of this invention comprises channel grooves in the form of a "T" or a "Y" having a central trunk and two branches etched into the surface of a silicon microchip, which surface is thereafter covered with a glass sheet. The central groove is formed of the trunk of the "T" or "Y", and the branches are the inlet means in fluid connection with the laminar flow channel for respectively conducting the sample and indicator streams into the laminar flow channel.

Channel cells of this invention may also include multiple inlet branches in fluid connection with the laminar flow channel for conducting a plurality of inlet streams into said channel. These may be arranged in a "candelabra"—like array or may be arranged successively along a "crossbar" for the "T" or the branches of the "Y" configuration, the only constraint being that laminar flow of all the streams must be preserved.

Inlet means include the inlet channels or "branches" and may also include other means such as tubes, syringes, and the like which provide means for injecting feed fluid into the device. Outlet means include collection ports, and/or means for removing fluid from the outlet, including receptacles for the fluid, means inducing flow by capillary action, pressure, gravity, and other means known to the art. Such receptacles may be part of an analytical or detection device.

Embodiments of the device of the present invention which allow for optical measurements in transmission are provided. In such embodiments, the channel cell system, or at least the analyte detection area, transects the width of the substrate plate in which the channel cell system is formed. Substrate plate as used herein refers to the piece of material in which the channel cell system of this invention is formed, e.g., a silicon wafer and a plastic sheet. The analyte detection area, and optionally other parts of the channel cell system, lie between optically transparent plates in a space which cuts through the entire width of the substrate plate. Analyte detection area as used herein refers to that portion of the indicator stream where analyte particles create a detectable change in the indicator stream.

Optical measurements exploiting reflected light are referred to herein as detection by reflection, whereas optical measurements exploiting transmitted light are referred to herein as detection by transmission.

A method is also provided for detecting the presence of analyte particles in a sample stream, preferably a liquid stream, also comprising larger particles comprising:
  a) conducting said sample stream into a laminar flow channel;
  b) conducting an indicator stream, said indicator stream preferably comprising an indicator substance which indicates the presence of said analyte particles, by a detectable change in property when contacted with particles of said analyte into said laminar flow channel, whereby said sample stream and said indicator stream flow in adjacent laminar streams in said channel;
  c) allowing analyte particles to diffuse into said indicator stream;
  d) detecting the presence of particles of the analyte in said indicator stream.

The flow rate of the input streams is preferably between about 5 micrometers/second and about 5000 micrometers/second, more preferably about 25 micrometers/second. Preferably the flow rate for both streams is the same.

The method and system of this invention include determining the concentration of the analyte particles in the sample stream by detecting the position within the laminar flow channel of analyte particles from the sample stream diffusing into the indicator stream causing a detectable change in the indicator stream or in an indicator substance in the indicator stream. The sample stream and the indicator stream may be allowed to reach equilibrium within the laminar flow channel. The location of the boundary of the detection area (i.e. that portion of the indicator stream containing diffused particles at a detectable concentration) with the unaffected indicator stream may be used to provide information about flow speed and/or sample concentration. The physical location of this boundary in the channel for a given analyte stays the same over time as long as the flow speed is constant and the sample unchanged. The location and size of the detection area can be varied by varying flow rate, sample concentration, and/or concentration of an indicator substance so as to optimize the signal for detection.

Information useful for determining the concentration of the analyte particles in the sample stream may be obtained by providing means for conducting specimen streams from the indicator stream at successive intervals along the length of the laminar flow channel, such as smaller channels equipped with viewports as described herein. Detection means such as those listed above are used to measure signals from the indicator stream. Changes in the intensity of the signals from specimen channel to specimen channel may be used to calculate the concentration of analyte particles in the original sample.

The method of one embodiment of this invention includes the use of an indicator substance which is immobilized on a particulate substrate carried within the indicator stream. The indicator substance is preferably a substance which changes in fluorescence or color in the presence of analyte particles, such as a dye, enzymes, and other organic molecules that change properties as a function of analyte concentration. The term "indicator substance" is also used to refer to polymeric beads, antibodies or the like having dyes or other indicators immobilized thereon. It is not necessary that the indicator stream comprise an indicator substance when detection means such as those directly detecting electrical, chemical or other changes in the indicator stream caused by the analyte particles are used.

Advantages of this system include the fact that analytes can be determined optically in turbid and strongly colored solutions such as blood, without the need for prior filtering or centrifugation; cross-sensitivities of indicator dyes to larger sample components (a common problem) can be avoided; and the indicator can be kept in a solution in which it displays its optimal characteristics (e. g., cross-sensitivities to pH or ionic strength can be suppressed by using strongly buffered solutions). Measurements of the indicator stream at several locations along the channel can compensate for some remaining cross-sensitivities. In addition, the flow channel can be wide, which makes it easy to measure the indicator fluorescence with simple optics. No membrane is needed; the system is less subject to biofouling and clogging than membrane systems. The system is also tunable in that sample or indicator stream concentrations and/or flow rates can be varied to optimize the signal being detected. For example, if a reaction takes about five seconds, the system can be adjusted so that the reaction will be seen in the central portion of the device.

The method can be conducted by a continuous flow-through of sample and indicator streams. The steady-state nature of this method makes longer signal integration times possible.

The sample stream may contain particles larger than the analyte particles which are also sensitive to the indicator substance. These do not diffuse into the indicator stream and thus do not interfere with detection of the analyte.

Additionally, a method for determining kinetic rate constants as a function of distance traveled by the sample stream and indicator stream from the T-joint where the two streams meet is provided. Generally, kinetic measurements are made by plotting a physical property related to concentration versus time, i.e., time of reaction. The method provided herein for making kinetic measurements as a function of distance traveled by the sample and indicator stream, rather than as a function of time, is advantageous for the following reasons. The constituents of the streams, i.e., the particles, and the concentrations thereof, at a given position in the flow channel remain constant, given that the flow rate is constant. This method allows for integrating the data from detection, e.g., optical measurements, over time, thereby increasing the accuracy of the data collected and hence of the calculated/determined rate constants. Furthermore, if an experimental error occurs during detection, e.g. in the collection of data, at a given time, one can merely perform the detection measurement again, at the distance/position in the flow channel where the error occurred. In prior art methods of making kinetic measurements, if data at a given time point are lost due to experimental error, those data cannot be collected again during the same experiment.

BRIEF DESCRIPTION OF THE DRAWINGS

FIG. 9, comprising

FIG. 10, comprising

DETAILED DESCRIPTION OF THE INVENTION

The microscale channel cells of this invention are useful to separate smaller particles from larger particles in a sample stream based on the fact that the diffusion coefficient of a particle is substantially inversely proportional to the size of the particle so that larger particles diffuse more slowly than smaller particles, on the fact that diffusion occurs more quickly at the microscale of this invention than in larger scale separation devices known to the art and on the fact that laminar, non-turbulent flow can be induced in adjacent streams at the microscale.

Figure 1:
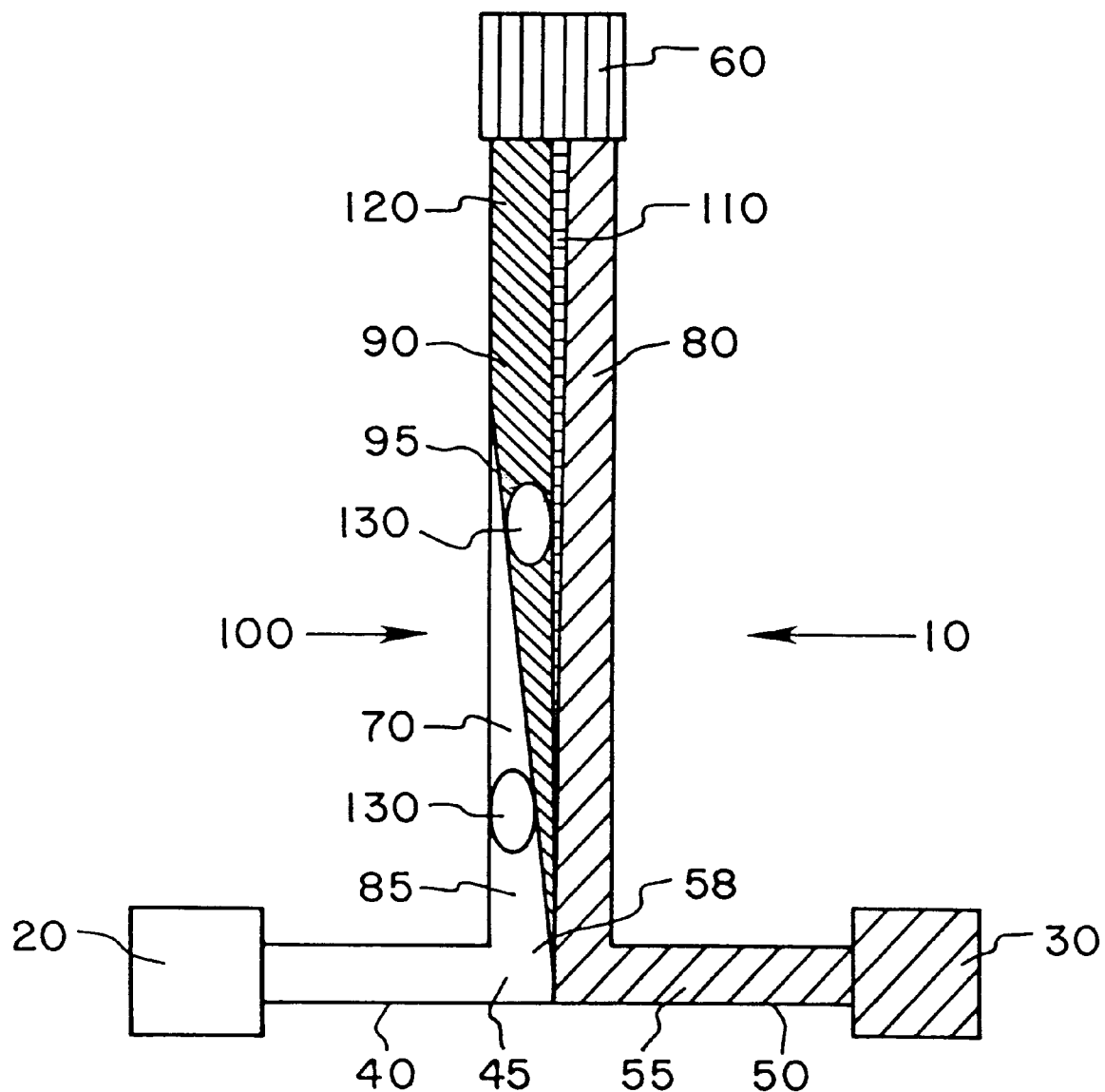
FIG. 1 is a schematic representation of flow and diffusion within the T-sensor channel cell embodiment of this invention.

As shown in FIG. 1, a channel cell in the form of a "T" is provided, referred to herein as T-sensor 10. The device can be microfabricated by etching on a silicon microchip. The geometry need not necessarily be a "T," as a "Y." Any angle that can be fabricated will also suffice. As discussed above, there may be a plurality of input channels. It is necessary only that all input channels merge into a single flow channel, and all channels be sufficiently small that laminar flow is preserved for all operating conditions. In general, the Reynolds number of the system is less than 1. The sample containing small molecules of interest, sample stream 80, is brought into the device through sample stream inlet port 30, from whence it flows into sample stream inlet channel 50, where it is referred to as sample inlet stream 55. An indicator stream 70 is brought into indicator stream inlet port 20, from whence it flows into indicator stream inlet channel 40, where it is referred to as indicator inlet stream 45.

Sample inlet stream 55 meets indicator inlet stream 45 at T-joint 58 at the beginning of flow channel 100, and the two streams flow in parallel laminar flow as indicator stream 70 and sample stream 80 to exit port 60. The indicator stream 70 contains an indicator substance such as a dye which reacts with analyte particles in the sample stream 80 by a detectable change in physical properties. Indicator stream 70 is shown in white in FIG. 1. Due to the low Reynolds number in the small flow channel 100, no turbulence-induced mixing occurs and the two streams flow parallel to each other without mixing. However, because of the short distances involved, diffusion does act perpendicular to the flow direction, so sample components (analyte particles) diffuse to the left into indicator stream 70 and eventually become uniformly distributed across the width of flow channel 100 at uniform analyte particle diffusion area 120.

The indicator stream 70 flows into flow channel 100 to form an initial reference area 85 into which analyte particles have not yet diffused. Analyte particles from sample stream 80 diffusing into indicator stream 70 form an analyte detection area 90 where analyte particles create a detectable change in the indicator stream 70, preferably by causing a detectable change in property in an indicator substance within the indicator stream 70. Particles of an indicator substance, e.g. dye particles, may also diffuse into sample stream 80 to form a diffused indicator area 110. If this change in local concentration of the indicator substance is a problem in some applications, its diffusion rate can be made arbitrarily small by immobilization on polymers or beads, e.g. indicator beads 130. In the T-sensor 10 of FIG. 1, a sample stream 80, e.g. blood, and an indicator stream 70 containing an indicator dye are joined at the intersection of sample stream inlet channel 50 and indicator stream inlet channel 40, with flow channel 100 (i.e., T-joint 58) and flow laminarly next to each other in flow channel 100 until they exit the structure at exit port 60. Small ions such as $H^+$ and $Na^+$ diffuse rapidly across the diameter of flow channel 100, whereas larger ions such as the dye anion diffuse only slowly. Larger particles such as sugars, proteins, and the like and blood cells show no significant diffusion within the time the indicator stream 70 and sample stream 80 are in contact with each other. The smaller sample components diffuse more rapidly and equilibrate close to the T-joint 58, whereas larger components equilibrate further up in flow channel 100. Furthermore, as the indicator has a particular half-saturation concentration ($pK_a$, in the case of a pH dye), a front or detection area boundary 95 of indicator dye color or fluorescence change exists as diffusion proceeds up the channel to form detection area 90. In practice the detection area boundary 95 and reference area 85 may form a curved line best seen in FIG. 2. The location and curvature of the front can have its "resting location" adjusted by changing flow speed and channel width to optimize signal size and intensity.

Although this is a flow system, the physical location of the detection area boundary 95 in flow channel 100 for a given analyte stays the same over time as long as the flows are constant and the sample unchanged. Analyte concentration is determined either by monitoring indicator signal at uniform analyte particle diffusion area 120 after substantial equilibration, or by noting the position of the front of steepest indicator color change, for example with a multi-element detector (see FIG. 3). The analyte detection area 90 can be as large as necessary to provide a detectable indicator signal. Similarly reference area 85 can be made to be as large as necessary to provide a detectable reference signal. Adjustments of these areas can be made as described below based on the diffusion coefficients of the analyte and indicator substance, flow rates and channel sizes.

Figure 2:
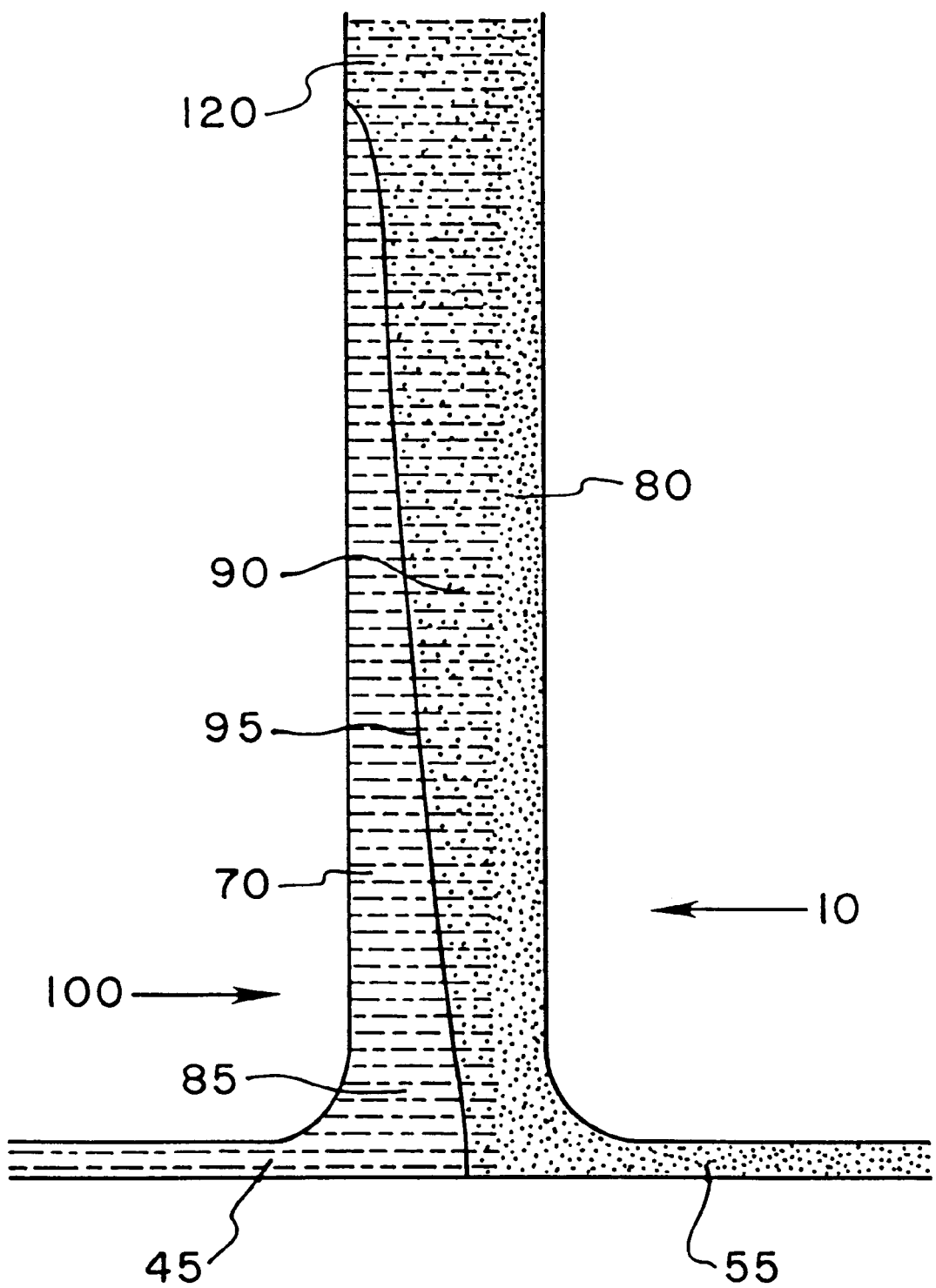
FIG. 2 is a fluorescence micrograph of a T-sensor of this invention in which a buffer solution of pH 9 (right inlet) is flowing into the device, and a weakly buffered indicator dye solution (pH 5) enters from the left. The distinct conversion of the dye from one form to the other as diffusion proceeds is clearly visible.

FIG. 2 shows a fluorescence microscope photograph of the T-sensor of FIG. 1 featuring an indicator inlet stream 45 which is a weakly buffered indicator dye solution of pH 5, and a sample inlet stream 55 which is a buffer solution of pH 9. The bright zone at the right is light reflecting on the silicon and does not relate to the sample and indicator streams. The sample stream 80 appears as a dark clear fluid on the right. The bright zone on the left is reference area 85 where analyte particles have not yet diffused into indicator stream 70. The grey area in the middle is analyte detection area 90 where $OH^-$ ions from the sample stream 80 have diffused into indicator stream 70 to form detection area 90. The fuzzy right edge of the grey detection area 90 is caused by dye particles diffusing into the sample stream 80. Uniform analyte particle diffusion area is shown at 120 where the $OH^-$ ions are uniformly diffused. The strongest signal is in the middle of detection area 90.

Figure 3:
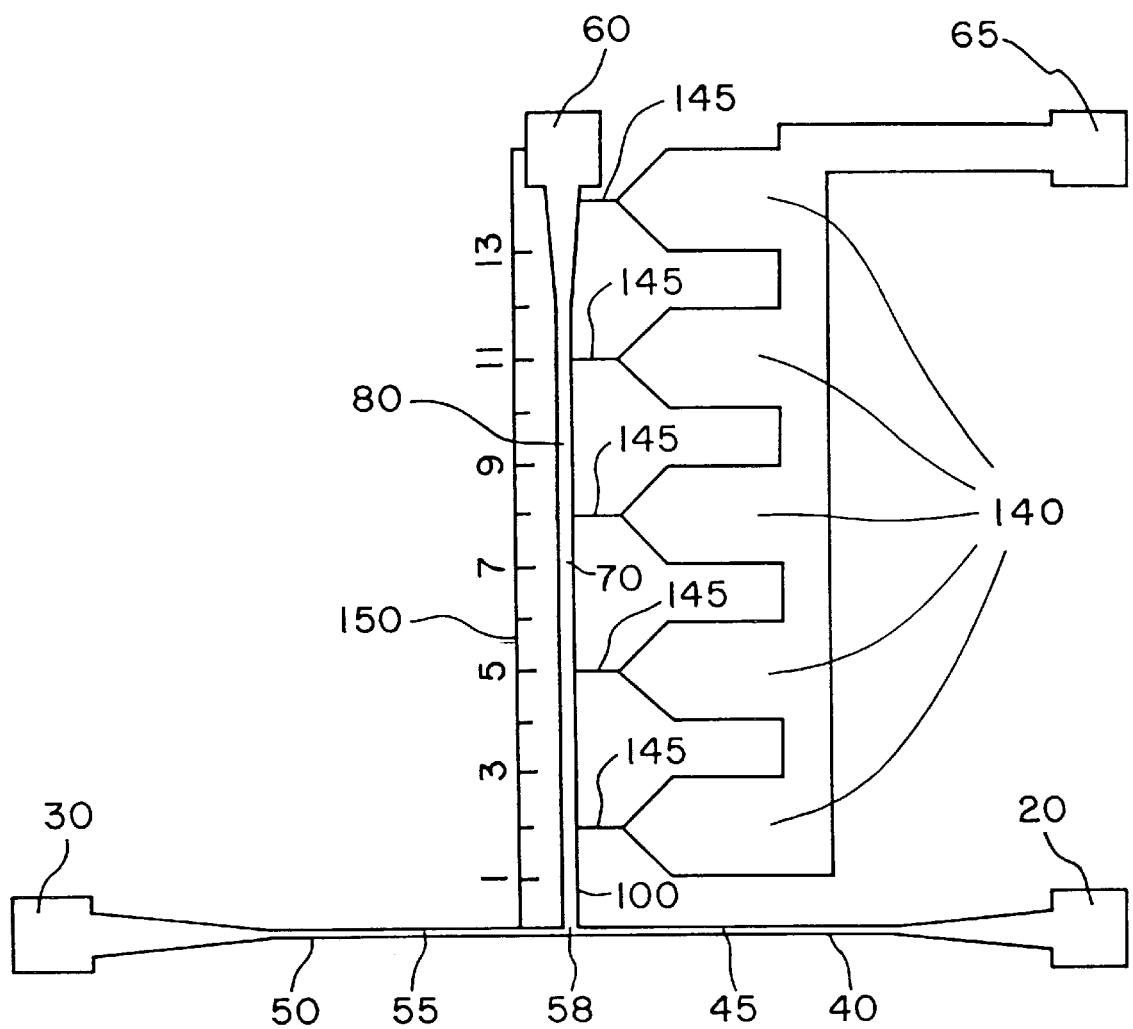
FIG. 3 shows the layout of the viewport-T-sensor embodiment of this invention. In this embodiment the indicator stream comes from the right T-leg, and is a solution of indicator dye in a low ionic strength buffer of pH 9. The sample stream, which is introduced from the left, here is a 0.15M buffer solution of pH 5. Several portions of the indicator stream which contains the indicator dye are continuously taken out of the channel as specimen streams at various locations.

FIG. 3 shows another embodiment of the T-sensor channel cell device of this invention having multiple specimen channels and viewports spaced along the length of the flow channel. In FIG. 3 an indicator inlet stream 45 enters from the right (rather than the left as in FIGS. 1 and 2) at indicator stream inlet port 20. A solution of indicator dye in a low ionic strength buffer of pH 9 is used. A sample inlet stream 55 which is a 0.15 M buffer solution of pH 5, enters from the left at sample stream inlet port 30. The concentration of the dye is only about 10% of the dye concentration used in FIG. 2. The indicator and sample streams 45 and 55 respectively, flow along indicator stream inlet channel and sample stream inlet channel 40 and 50 respectively, to meet at T-joint 58 and flow laminarly together along flow channel 100. Specimen streams 145 from indicator stream 70 which contain the indicator dye are continuously taken out of flow channel 100 at various locations. These specimen streams 145 flow through widenings which serve as viewports 140. Due to the size of the viewports 140 (several square millimeters), the fluorescence intensity can be easily monitored through a fluorescence microscope, or directly with a photodetector.

The viewport closest to T-joint 58 contains mainly undisturbed dye solution, whereas the viewport closest to exit port 60 contains the sample stream 80 completely equilibrated with the indicator stream 70. The viewports in between contain the indicator stream 70 in various degrees of equilibration with the sample components. The closer to T-joint 58, the more likely the viewport is to contain only small ions from the sample. A fluorescence micrograph of the viewports shows that the color in the viewport closest to T-joint 58 is the red color of the base form of the undisturbed indicator dye, whereas the yellow-green color of the viewports closest to exit port 60 represent the acid form of the dye, after the pH of the indicator stream 70 was altered from basic to acidic when diffusion-based equilibration has been reached.

The viewport T-sensor of FIG. 3 lends itself to simple referencing techniques. The integral fluorescence intensity of each viewport at one or more wavelengths can easily be measured through a fluorescence microscope, or directly, with photodiodes. In the easiest case, with an indicator dye showing no cross-sensitivity to other sample components, the intensity ratio between selected viewports gives a measurement value largely independent of dye concentration and excitation light intensity. Measuring at more than one viewport increases the redundancy and therefore the measurement accuracy.

In cases of cross-sensitivity of the indicator to larger sample components (e.g. larger biomolecules such as albumin), this interference can be referenced out by comparing the ratios of the different viewports. The viewports closer to T-joint 58 will contain mainly smaller sample components, whereas the viewports further up flow channel 100 will also contain larger particles.

The T-sensor device of the present invention can be used with reporter beads to measure pH, oxygen saturation and ion content, in biological fluids. (U.S. patent application Ser. No. 08/621,170, now U.S. Pat. No. 5,747,349, "Fluorescent Reporter Beads for Fluid Analysis," which is incorporated by reference herein in its entirety, discloses fluorescent and absorptive reporter molecules and reporter beads.) Reporter beads can also be used to detect and measure alcohols, pesticides, organic salts such as lactate, sugars such as glucose, heavy metals, and drugs such as salicylic acid, halothane and narcotics. Each reporter bead comprises a substrate bead having a plurality of at least one type of fluorescent reporter molecules immobilized thereon. Plurality as used herein refers to more than one. A fluorescent property of the reporter bead, such as intensity, lifetime or wavelength, is sensitive to a corresponding analyte. Reporter beads are added to a fluid sample and the analyte concentration is determined by measuring fluorescence of individual beads, for example, in a flow cytometer. Alternatively, absorptive reporter molecules, which change absorbance as a function of analyte concentration, can be employed. The use of reporter beads allows for a plurality of analytes to be measured simultaneously, and for biological cells, the cell content can also be measured simultaneously. A plurality of analytes can be measured simultaneously because the beads can be tagged with different reporter molecules.

The fluorescent reporter molecules of this invention can be any fluorescent molecules having fluorescence properties which are a function of the concentration of a particular analyte or class of analytes. Many dyes and fluorochromes known in the art can be used as reporter molecules in this invention (see, for example, R. P. Haugland, Handbook of Fluorescent Probes and Research Chemicals, 5th Edition, Molecular Probes Inc., Eugene, 1992). The criteria for reporter molecule selection are that the molecules can be immobilized on a substrate bead and that their fluorescence is a function of the concentration of an analyte. In contrast with previously used fluorescent beads, wherein the number of beads in an aggregate changes, the reporter beads of U.S. patent application Ser. No. 08/621,170 are not required to have an immunoreagent, such as a ligan, antiligand, antigen or antibody, on the surface in combination with the reporter molecules.

Fluorescent reporter molecules interact with the analyte in a way that changes the fluorescent properties of the reporter molecule. In some instances the reporter molecule reacts with the analyte, as in the case of albumin detection by AB 580 (Molecular Probes). In some cases the interaction is not a chemical reaction. For example the reporter molecule fluorescence can be quenched by nonradiative energy transfer to the analyte, as in the case of $O_2$ detection by ruthenium diphenyl phenanthroline. For some reporter molecules the fluorescence is sensitive to polarity changes in the fluid, which can be used to detect organic solvents and hydrocarbons within an aqueous fluid. The interaction can also be through other solvent effects, wherein the ionic strength of the solvent affects the fluorescence. Solvent effects can be used to determine the total concentration of all dissolved ions. The interaction can be a ligand/antiligand or antigen/antibody reaction. The interaction preferably does not lead to an aggregate with other particles and, in particular, does not create an aggregate containing a plurality of reporter beads. It is preferred that the interaction of the analyte with the reporter molecules does not significantly perturb the analyte concentration in the fluid.

In the case of fluorescent reporter beads, at least one fluorescence property of the reporter molecules is a function of analyte concentration. The property measured for the reporter beads can be any property which is affected by the analyte interaction with the beads, such as the fluorescence intensity, decay time or spectrum.

Alternatively, the reporter molecules can be absorption indicators, for example the physiological pH indicator N9 (Merck, Germany) immobilized on a substrate bead. Such indicators change their absorption as a function of analyte concentration. Typically the color of the molecules changes (i.e., the wavelength of their absorption maximum changes).

Absorptive reporter molecules can be used in combination with fluorescent reporter molecules on a substrate bead, and absorptive beads can be used in combination with fluorescent beads.

The substrate bead function is to allow the detection of an analyte, and optionally its concentration, with optical measurements of single beads. More than one type of reporter bead, i.e., beads with different reporter molecules immobilized thereon, can be used to analyze a given sample, provided that the bead type can be identified. Beads can be identified by various means, including means employing bead size, e.g., light scattering; fluorescent tag(s) attached to the bead which has a different excitation and/or emission wavelength from that of the fluorescent reporter molecule attached to that bead; or by directly identifying the fluorescent molecule attached to the bead. This allows for detection of more than one analyte at a time. The substrate bead also functions to immobilize the reporter molecules to prevent their diffusion into the sample stream. The reporter molecules can be on the surface of or within the substrate bead. The beads can be fabricated from a variety of materials and can have any shape, not limited to spherical. Suitable materials include glass, latex, hydrogels, polystyrene and liposomes. The beads can have added surface groups to facilitate attaching reporter molecules, such as carboxyl groups on latex and amino-modified polystyrene.

Various techniques can be employed to immobilize the reporter molecules on the substrate bead. Adsorption based coatings can be prepared by immersing the substrate beads in a reporter molecule solution and then washing off excess reporter molecules. Reporter molecules can similarly be diffused into the cavity of controlled pore glass beads. Reporter molecules can also be covalently immobilized by chemically attaching them to functional groups of suitable substrate beads. Polymerized beads can be formed in a solution containing reporter molecules, thereby trapping the molecules in a fixed polymer cavity. To immobilize reporter molecules in a liposome, lipids can be mixed with a reporter molecule solution, the solution shaken, and the liposomes separated.

To employ reporter beads in the methods of this invention, the beads are mixed with a fluid sample and the fluorescence or absorption of individual beads is measured. The beads can be dry before mixing with the sample or can be dispersed in a fluid. For microscale measurements it is preferred that the added volume of beads and any accompanying fluid be small compared to the sample volume (for example <1%) so that sample dilution is insignificant.

The channel cells of this invention may be formed by any techniques known to the art, preferably by etching the flow channels onto the horizontal surface of a silicon microchip and placing a lid, preferably of an optically clear material such as glass or a silicone rubber sheet, on the etched substrate. Other means for manufacturing the channel cells of this invention include using silicon structures or other materials as a template for molding the device in plastic, micromachining, and other techniques known to the art. The use of precision injection molded plastics to form the devices is also contemplated. Microfabrication techniques are known to the art, and more particularly described below.

In a preferred embodiment of this invention, channel cells of this invention have hydrophilic surfaces to facilitate flow of liquid therein and allow operation of the device without the necessity for pressurization. The substrate may be treated by means known to the art following fabrication of the channels, to render it hydrophilic. The lid is also preferably treated to render it hydrophilic.

The T-sensor channel system of this invention can be in fluid connection with one or more v-groove channels. A silicon microchip can be etched to form a v-groove with reflective surfaces/walls of the channels. Thus, optical measurements can exploit reflected, rather than transmitted, incident light. Detection can be achieved by reflection, that is by detecting reflected light. Small angle scattered light (scattered off the surfaces of any particles in the channel) is also reflected by the v-groove wall and can be collected by a small angle photodetector. Large angle scattered light and fluorescent light can exit the channel without reflection and can be collected by the a large angle photodetector. In addition, the reflective wall of the v-groove behind the illuminated particle enhances the fluorescence collection efficiency. Any part of the incident light, e.g., laser beam, that is not within the v-groove channel is reflected from the silicon surface in a direction away from either the small or large angle detectors. The fraction of light reflected from the lid, e.g., transparent cover plate, in a case wherein light enters from air without being directly coupled into the lid/cover plate, is also directed away from the small and large angle detectors thereby reducing undesirable background light intensity from the measurements.

Because the v-groove flow channel reflects the incident light, rather than transmitting it, fabrication of the microchannel system of this invention is extremely simple. The microchannel is fabricated from a single microchip of silicon which is patterned on a single side. A transparent cover plate is attached to the top of the microchip to seal the channel.

Figure 4:
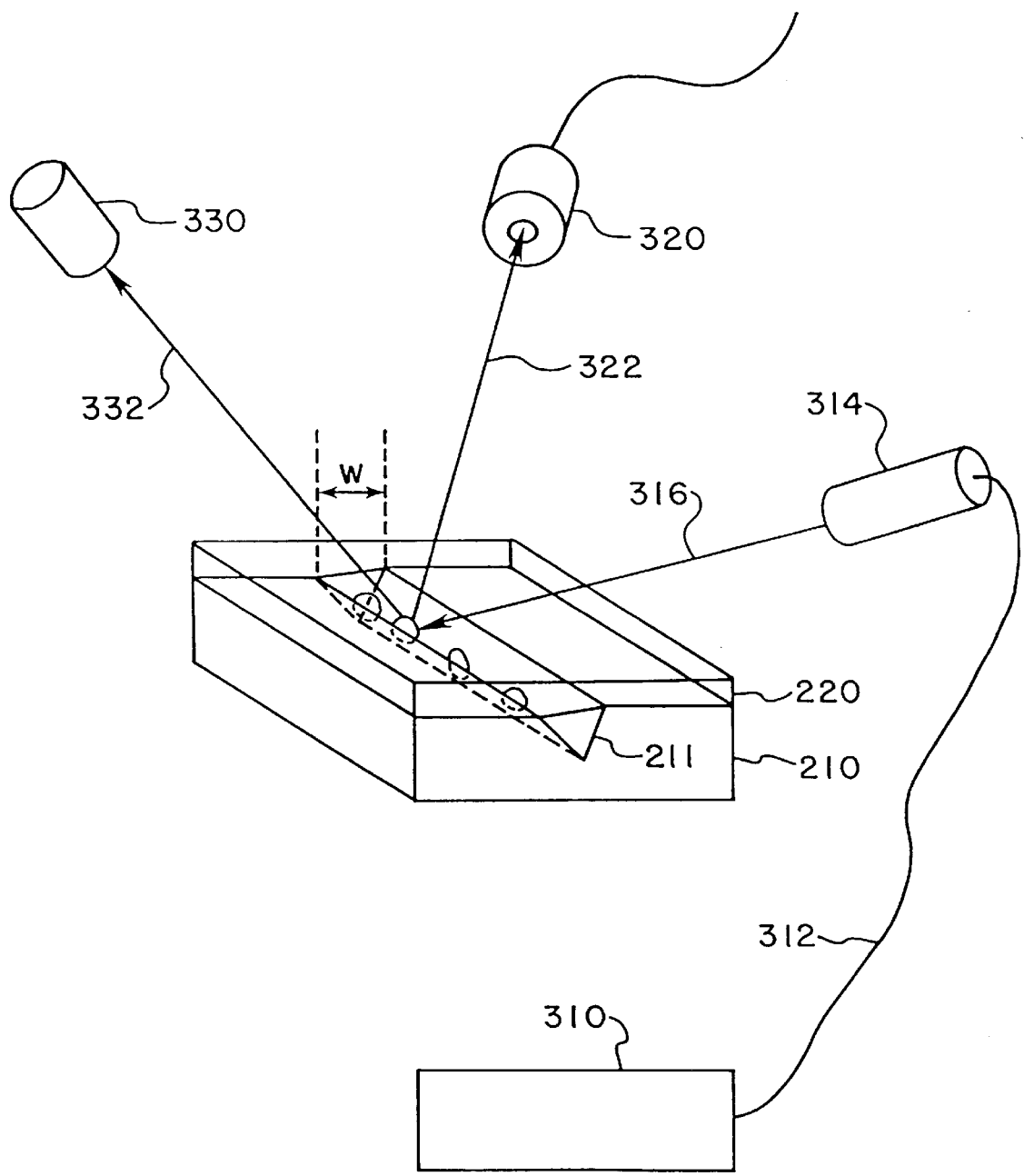
FIG. 4 shows a v-groove flow channel coupled with a flow cytometer optical head.

FIG. 4 shows a v-groove flow channel and optional optical head. Silicon microchip 210 has v-groove 211 therein. The term v-groove is used herein for a substantially "V" shaped groove in the surface of a silicon microchip. Depending on the fabrication process the point of the "V" can be flat ( a trapezoidal groove), but only if the flat portion does not fall within the analyte detection area defined by the interception of the illumination beam with the sample flow. In a preferred embodiment, microchip 210 has a <100> surface orientation and the walls of groove 211 are along <111> planes, providing an angle of 54.7° between the walls of the groove and the plane of the surface of the microchip. Transparent cover plate 220 is sealed to the surface of microchip 210. In a preferred embodiment the cover plate is made of pyrex and is anodically bonded to the silicon microchip. In the illustrated embodiment the light source includes diode laser 310, optical fiber 312 and focusing head 314. Non-scattered light, i.e., light which has not been scattered by a particle, is specularly reflected by a wall of channel 211 and travels along path 322. Small angle (forward) scattered light deviates slightly from path 322 and impinges on small angle detector 320. Some of the light scattered at large angles travels along path 332 to large angle photodetector 330. The photodetectors can be photodiodes or photomultipliers. Large angle detector 330 can be used to measure large angle scattering and/or fluorescence.

Means for applying pressure to the flow of the feed fluids through the device can also be provided. Such means can be provided at the feed inlets and/or the outlet (e.g. as vacuum exerted by chemical or mechanical means). Means for applying such pressure are known to the art, for example as described in Shoji, S. and Esashi, M. (1994), "Microflow devices and systems," J. Micromechanics and Microengineering, 4:157–171, and include the use of a column of water or other means of applying water pressure, electroendoosmotic forces, optical forces, gravitational forces, and surface tension forces. Pressures from about $10^{-6}$ psi to about 10 psi may be used, depending on the requirements of the system. Preferably about $10^{-3}$ psi is used. Most preferred pressures are between about 2 mm and about 100 mm of water pressure.

An example of an embodiment using multiple streams is a channel cell having three inlet streams flowing in laminar flow wherein the middle stream is a reagent stream. For example, the sample stream may be blood, the middle stream glucose oxidase, and the third stream an indicator stream containing pH sensitive dye. As glucose particles diffuse through the reagent stream they are changed to gluconic acid which is detected by a pH-sensitive dye when the gluconic acid molecules diffuse into the indicator stream. Other examples of multiple-stream systems include systems having several sample streams with analyte at different concentrations for calibration of the detection means. Indicator streams not adjacent to the sample streams may also be used as control streams.

The indicator stream can be measured by the detection means before and after diffusion of particles into the stream has taken place, and such measurements as well as the rate of change of the indicator stream along its length can be used to assay analyte concentration. In addition, multiple detection means of different types can be used to measure the indicator stream. Field effects which are ion or chemical sensitive can be measured at different locations in the device.

The channel cells of this invention and the channels therein can be sized as determined by the size of the particles desired to be detected. As is known in the art, the diffusion coefficient for the analyte particles is generally inversely related to the size of the particle. Once the diffusion coefficient for the particles desired to be detected is known, the contact time of the two streams, size of the central channel, relative volumes of the streams, pressure and velocities of the streams can be adjusted to achieve the desired diffusion pattern.

Fluid dynamic behavior is directly related to the Reynolds number of the flow. The Reynolds number is the ratio of inertial forces to viscous forces. As the Reynolds number is reduced, flow patterns depend more on viscous effects and less on inertial effects. Below a certain Reynolds number, e.g., 0.1, inertial effects can essentially be ignored. The microfluidic devices of this invention do not require inertial effects to perform their tasks, and therefore have no inherent limit on their miniaturization due to Reynolds number effects. The devices of this invention require laminar, non-turbulent flow and are designed according to the foregoing principles to produce flow having low Reynolds numbers, i.e. Reynolds numbers below about 1.

The Reynolds number is the ratio of inertial forces to viscous forces. As the Reynolds number is reduced, flow patterns depend more on viscous effects and less on inertial effects. Below a certain Reynolds number, e.g. below about 1, (based on lumen size for a system of channels with bends and lumen size changes), inertial effects can essentially be ignored. The microfluidic devices of this invention do not require inertial effects to perform their tasks, and therefore have no inherent limit on their miniaturization due to Reynolds number effects. Applicants' channel cell designs, while significantly different from previous reported designs, operate in this range. These microfluidic devices of this invention require laminar, non-turbulent flow and are designed according to the foregoing principles to produce flows having low Reynolds numbers.

The devices of the preferred embodiment of this invention are capable of analyzing a sample of a size between about 0.01 microliters and about 20 microliters within a few seconds, e.g. within about three seconds. They also may be reused. Clogging is minimized and reversible. The sizes and velocities of 100 µm wide and 100 µm/s, for example, indicate a Reynolds number ($R_3$=plv/η) of about $10^{-2}$ so that the fluid is in a regime where viscosity dominates over inertia.

The magnitude of the pressure drop needed to obtain an average velocity, v, of a fluid with absolute viscosity, η, and density, p, through a circular channel (length, l, diameter, d) can be calculated from Poiseuille's Law (Batchelor, G. K., *An Introduction to Fluid Dynamics,* Cambridge Univ. Press 1967), $$\frac{P}{l} = \frac{32\eta v}{d^2}$$

Using v=100 µm/sec and d=100 µm, we get a pressure drop equivalent to about 0.3 mm of $H_2O$ per cm of channel length. Since Poiseuille's equation is strictly valid only for circular flow channels and the channels of this invention are substantially rectangular in cross-section it can be considered only as an approximate relation between the variables represented.

When a liquid is introduced into a device there is at first an effective pressure, $P_{eff}=P_0+P_{st}$, equal to the sum of the applied pressure, $P_0$, and a pressure due to the surface tension, $$P_{st} = \frac{\gamma \cos \Theta}{r}.$$

$P_{st}$ is a function of the surface tension of the fluid, γ, the contact angle of the fluid with the surface, θ, and the radius of curvature of the fluid surface, r.

For hydrophilic surfaces, cos θ is close to 1, and for small channels no applied pressure is needed to wet the device. This is referred to as "wetting by capillary action." However, once the device is completely wet, one has to worry about the surface tension at the exit area. In the device described in the example hereof, the radius of curvature of the fluid in the exit area was several millimeters, so that the pressure due to the surface tension was negligible With a channel width of 100 µm, $P_{st}$ is about 1 cm of $H_2O$, so surface tension on the exit channel is significant. However, using an etchant such as EPW F-Etch as described below, which attacks the <100> planes of silicon, means that the corners as etched are not as sharp as shown in the figures. This results in a gradual widening of the channel to about 1 mm which reduces the effect of the surface tension.

By adjusting the configuration of the channels in accordance with the principles discussed above to provide an appropriate channel length, flow velocity and contact time between the sample stream and the indicator stream, the size of the particles remaining in the sample stream and diffusing into the indicator stream can be controlled. The contact time required can be calculated as a function of the diffusion coefficient of the particle D and the distance d over which the particle must diffuse by $t=d^2/D$. Particles or molecules that have diffusion coefficients larger than D will diffuse into the indicator stream, and particles or molecules having a diffusion coefficient substantially smaller than D will not. If the diffusion coefficient of the larger particles is about ten times smaller than D, the indicator stream should be entirely free of the large particles.

Figure 5:
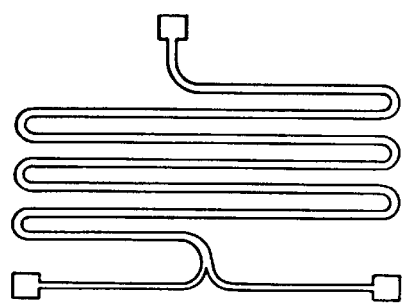
FIG. 5 shows a convoluted flow channel in a square wave shape.
Figure 6:
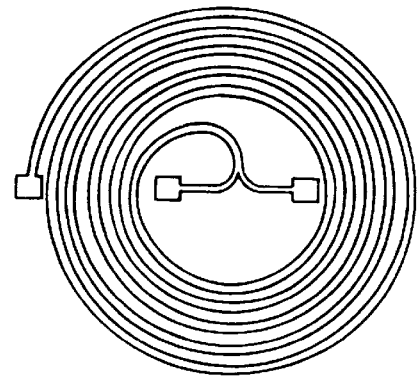
FIG. 6 shows a convoluted flow channel in a coiled shape.

For a given flow speed, some analytes with relatively small diffusion coefficients, a straight channel cell system (T-sensor) channel, preferably 5–50 mm in length, does not provide a long enough flow channel for diffusion to occur adequately. Typically, silicon microchips are 3 inches, 4 inches, 6 inches, or 8 inches in diameter. A straight channel etched into a microchip of such size can be no longer than the microchip diameter. Detection of analytes with relatively small diffusion coefficients, e.g. relatively large analytes or non-spherical analytes, preferably employs a convoluted flow channel. A convoluted flow channel as used herein refers to a flow channel which is not straight. FIGS. 5 and 6 show two different channel geometries which allow for longer flow channels on a typical 3–4 inch silicon microchip.

In the channel cell system (T-sensor) of FIG. 5, the left and right streams, e.g., sample and indicator streams, have the same overall pathlength. If multiple measurements are taken in this embodiment, they should be taken along the vertical center line of the sensor so that both streams are flowing at the same flow speed and have had the same flow distance. In this embodiment, wherein the convoluted flow channel has a square wave shape like that in FIG. 5, the streams flow at different speeds through the curves. Therefore, it may be preferable to use slower flow speeds than the speeds used in straight flow channels because the tight/narrow curves and sheer forces between the streams flowing at different speeds can cause zones in which laminar recirculation occurs. Laminar recirculation is not turbulence; the flow is still laminar and predictable. Nonetheless, laminar recirculation is not preferable and can be avoided by maintaining a Reynolds number below about 1.

The channel cell system (T-sensor) of FIG. 6 shows a coiled/spiral flow channel. In this geometry, four separate T-sensors each having a 220 mm long flow channel, can be fabricated on a single 3 inch microchip. Because the bending radius is larger in this geometry than in the square wave geometry, laminar recirculation is less likely to occur. The difference in relative flow speeds of the left and right streams (sample and indicator streams) is minimal, leading to less sheer stress between the two streams if the two streams have different viscosities. This channel geometry does, however, create different overall flow distances for the left and right streams.

Figure 7A:
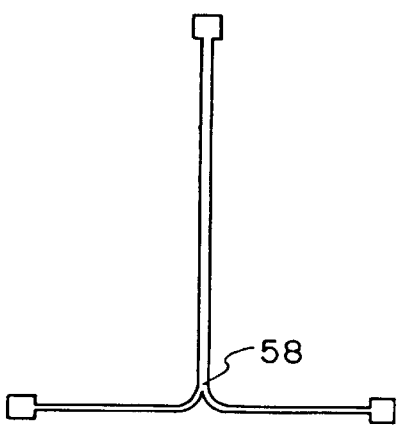
FIG. 7A shows a T-sensor with a rounded T-joint.
Figure 7B:
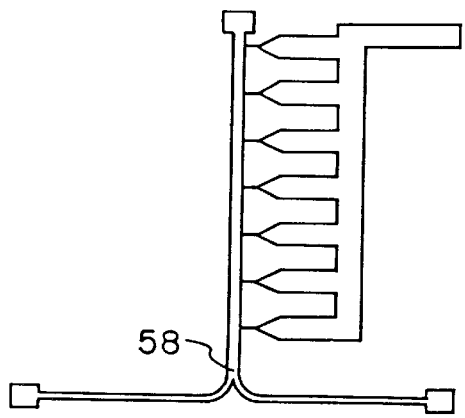
FIG. 7B shows a viewport-T-sensor with a rounded T-joint.

FIGS. 7A and 7B illustrate channel cell systems (T-sensor devices) of this invention wherein the T-joint 58 is rounded. FIG. 7A shows a T-sensor similar to the one shown in FIG. 1, except that the T-joint 58 is rounded in FIG. 7A. FIG. 7B shows a viewport T-sensor similar to the one shown in FIG. 3, except that the T-joint 58 is rounded in FIG. 7B. A rounded T-joint is preferable because it helps prevent laminar recirculation in the T-joint which can occur at Reynolds number above about 1. A rounded T-joint is preferable also because it decreases the chance of contamination of the sample stream with the indicator stream, and vice versa.

The channel cell system of this invention can be used to measure concentration of an analyte as a function of distance (from the T-joint) rather than time. An increment of distance is proportional to an increment of time. With laminar flow and a known flow speed, an increment of distance can be converted to an increment of time.

Other methods for making kinetic measurements employ plotting concentration, or some physical property resulting from concentration, e. g., absorbance or fluorescence, versus time. The decrease in concentration of a starting material, or increase in concentration of a product, with time determines the kinetic rate constant for a reaction.

Figure 8:
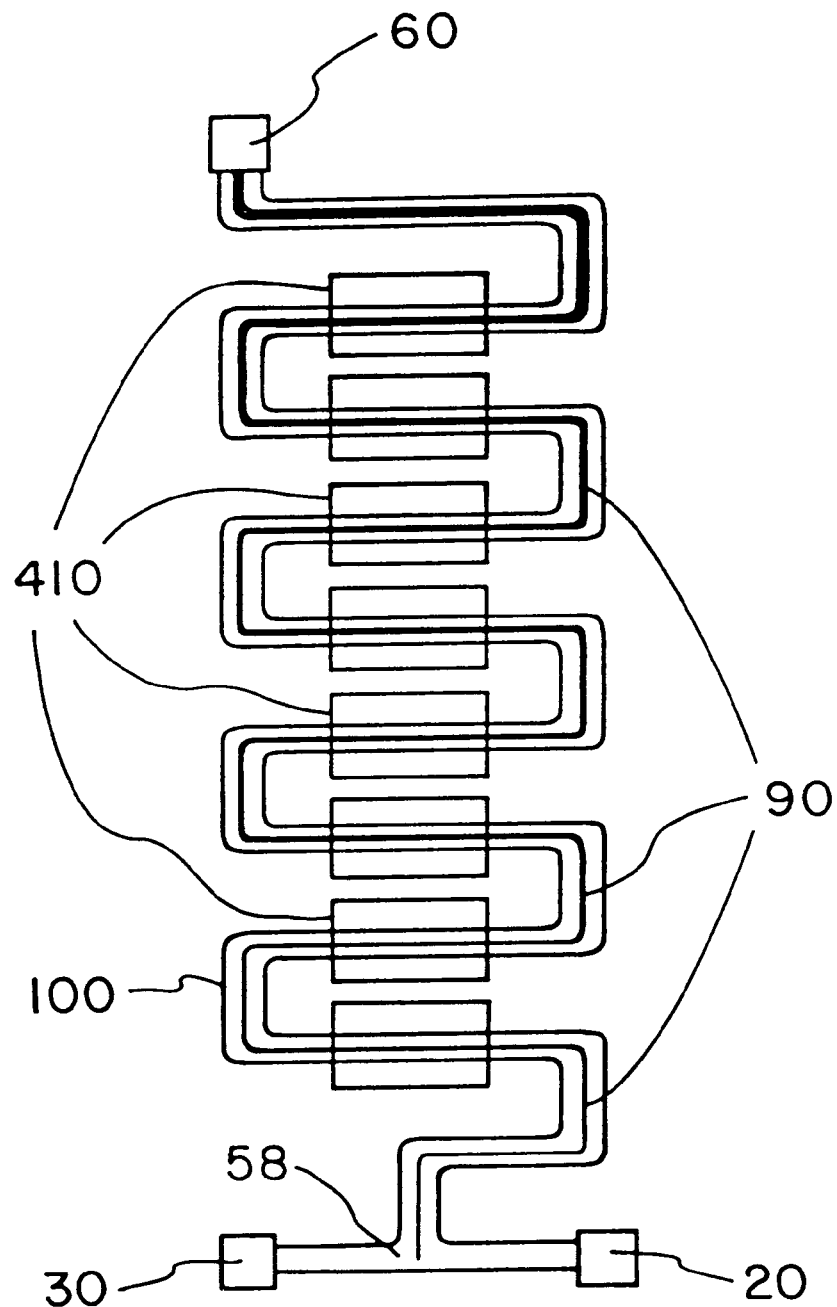
FIG. 8 shows a convoluted flow channel with a plurality of detection areas for making kinetic measurements as a function of distance.

The rate of, or rate constant for, a reaction can be determined using the T-sensor device of this invention. Detection, e.g., absorption or fluorescence measurements, can be performed at one or more analyte detection area. Referring to FIG. 8, a plurality of analyte detectors 410 can be positioned at various distances from the T-joint 58. Alternatively, one detector can be used to monitor the flow channel at various distances from the T-joint 58. FIG. 8 shows a square-wave/serpentine shaped flow channel. However, a T-sensor of any geometry which maintains laminar flow can be employed to make kinetic measurements, particularly according to the methods disclosed herein. A sample stream is introduced via sample stream inlet port 30 and an indicator stream is introduced via indicator stream inlet port 20. The two streams meet at T-joint 58. Analytes from the sample stream begin to diffuse into the indicator stream, and a measurable change, e.g., increase in fluorescence, occurs. A measurable change occurs as a result of analytes diffusing into the indicator stream, shown at analyte detection areas 90.

The intensity of fluorescence or absorbance in the analyte detection area and the width of the analyte detection area are measured at various distances from the T-joint 58. The intensity and width of the analyte detection area are a function of the concentration of the analyte being measured. As the analyte diffuses into the indicator stream, a change in color (i.e. change in optical absorbance) or fluorescence occurs in the analyte detection area. This optical change becomes more intense with increasing distance from the T-joint, because the analyte and the indicator have had a longer time to interact with each other. The width of the analyte detection area also increases with increasing distance from the T-joint. Two independent causes lead to this increase in width. First, the analytes diffuse farther with increasing time, and therefore with increasing distance. Second, the more the interaction between the analyte and indicator has progressed, the greater the absorbance or fluorescence at the analyte detection area. Hence, absorbance or fluorescence can be detected at a greater width in the analyte detection area.

Referring to FIG. 8, the analyte detection area 90 becomes wider and more intense with increasing distance from the T-joint 58.

Using the device and methods of this invention, a rate constant for a reaction can be determined with as few as one measurement, e.g., fluorescence at a certain distance from the T-joint. As is known in the art, increasing the number of measurements leads to increased accuracy of the kinetic rate constant calculated from such measurements.

Figure 9A:
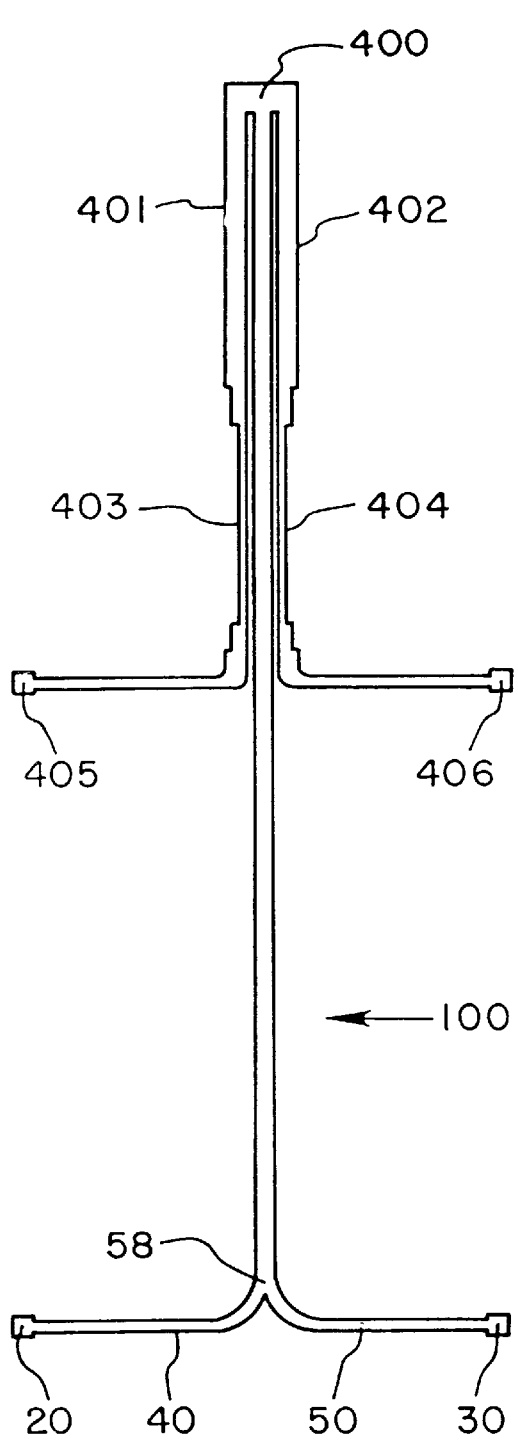
FIGS. 9A–9C, shows embodiments with branching flow channels for dual detection of both dissolved and undissolved analytes.
Figure 9B:
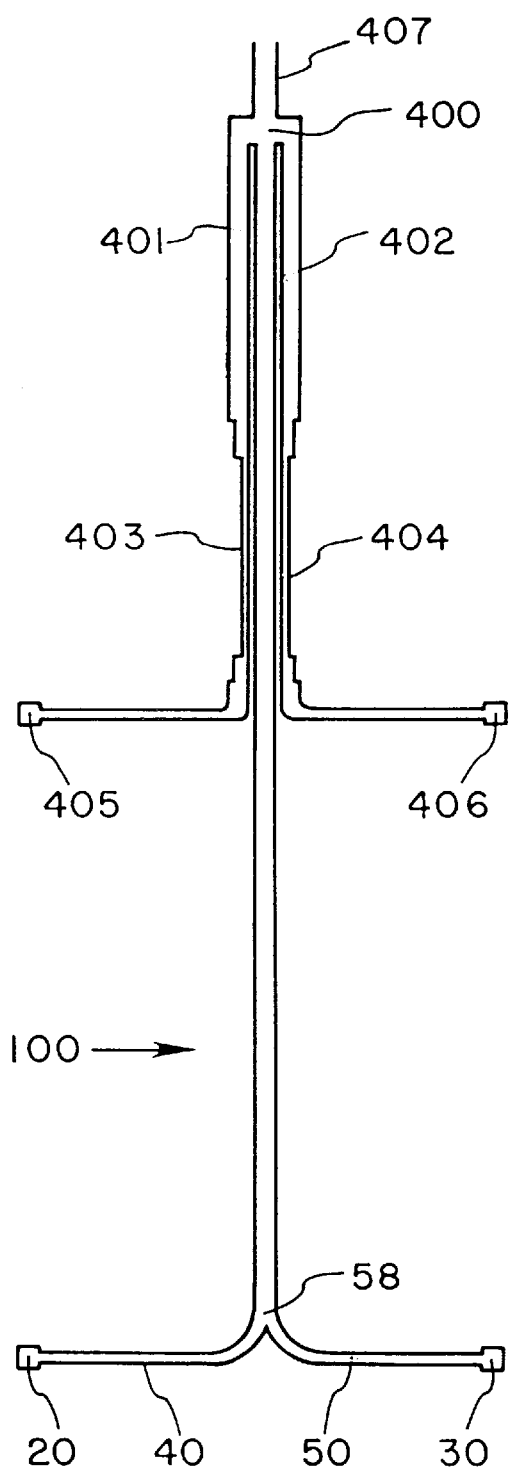

In another embodiment, the T-sensor channel cell system of this invention can comprise branching flow channels 401 and 402 as illustrated in FIG. 9A. The sample containing small molecules of interest is brought into the device through sample stream inlet port 30, from whence it flows into sample stream inlet channel 50. An indicator stream is brought into indicator stream inlet port 20, from whence it flows into indicator stream inlet channel 40. The two streams flow parallel to one another in laminar flow, and small molecules (analytes) from the sample stream diffuse into the indicator stream. Branching flow channels as used herein refer to flow channels in fluid connection with the flow channel 100. A W-joint 400 as shown in FIGS. 9A and 9B may be used to correct the branching flow channels 401 and 402 with flow channel 100. Branching flow channels allow for detection of both undissolved and dissolved particles. A detector, preferably positioned above or below the device, monitors the flow channel 100 and v-grooves 403 or 404. This dual detection embodiment can detect dissolved and undissolved particles in the flow channel 100 as well as undissolved particles flowing in single file fashion in the v-groove(s). Particle detection can be performed by standard optical techniques, e.g., imaging, light scattering, or spectroscopy, as the particles flow through one or both of the v-grooves 403 or 404, which are in fluid connection with branching flow channels 401 and 402, respectively. Branching flow channels 401 and 402 are in fluid connection with exit ports 405 and 406, respectively.

For example, in this embodiment a sample, e.g., whole blood, can be introduced via sample stream inlet port 30 from whence it flows into sample stream inlet channel 50 and a buffered solution containing reporter beads can be introduced via indicator stream inlet port 20 from when it flows into indicator stream inlet channel 40. The sample and indicator stream flow parallel to each other in laminar flow in flow channel 100. Small analytes in the sample, e.g., protons, diffuse into the indicator stream. Referring to FIG. 9A, the sample flows into branching flow channel 402 and then into v-groove 404, through which particles, e.g., red and white blood cells, flow in single file fashion. At the same time, the reporter beads flow into branching flow channel 402 and then into v-groove 403, through which the beads flow in single file fashion. An optical detector, preferably positioned above or below the device simultaneously monitors the two streams in flow channel 100 and the undissolved sample particles in v-groove 404 and beads in v-groove 403, the beads being indicators of dissolved sample analytes.

Alternatively, the indicator stream can include a dissolved indicator dye which is monitored with the monitoring of the undissolved sample particles when this embodiment of the present device is employed. A dissolved indicator dye does not need to be monitored in a v-groove. Hence, both branching flow channels need not be connected to v-grooves, as illustrated in FIG. 9C.

Another example of the dual detection embodiment of this invention is the following. A sample of whole blood can be monitored in a v-groove channel to detect the number of white blood cells. Then the same sample flows into a T-sensor in fluid connection with the v-groove channel. In the T-sensor the white blood cells react with fluorescent reporter beads tagged with an antibody. Then the sample flows into another v-groove channel in fluid connection with the T-sensor. In this v-groove channel the white blood cells are identified by fluorescence.

The T-sensor channel system of the present invention can further comprise a waste port 407, as illustrated in FIG. 9B. To insure that only sample stream enters branching flow channel 402, and that only indicator stream enters branching flow channel 401, a portion of each stream can be diverted to a waste port 407. The waste port is in fluid connection with the flow channels at the W-joint to divert a portion of each stream to a waste outlet.

Figure 9C:
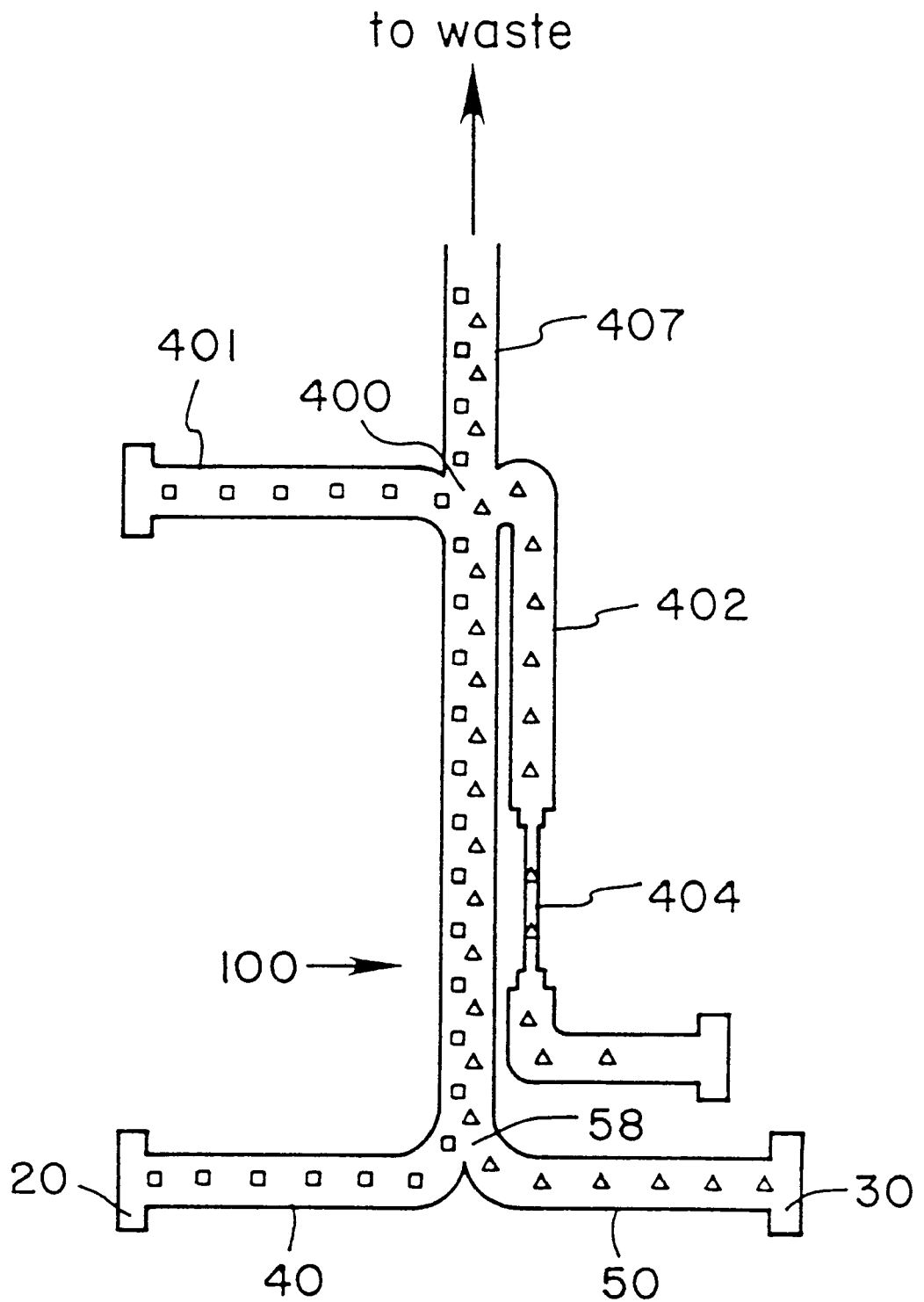

FIG. 9C illustrates sample stream (represented by x) and indicator stream (represented by squares) flowing through the channel system of this invention comprising branching flow channels and a waste port. FIG. 9C further illustrates that the branching flow channels do not have to loop back and run parallel to the flow channel 100. Branching flow channels can connect to the flow channel 100 in any angle desired. In order to monitor the flow through the various channels simultaneously and with one detector it is preferable that the branching flow channels connect with the flow channel 100 at an angle which allows for such monitoring.

Detection of dissolved and undissolved particles in one device employing this embodiment is economically advantageous, as measurements can be performed with only one set of pumps and one detector.

Another means for detecting undissolved particles in single file flow employs a sheath flow module. A sample can first flow through a flow channel of a T-sensor where the sample reacts with reporter beads, e.g., an analyte in the sample diffuses into an indicator stream containing reporter beads. The fluid containing reporter beads can then flow into a sheath flow module in fluid connection with the T-sensor flow channel. In the sheath flow module the beads are focused so that they flow in single file fashion for detection.

Figure 10A:
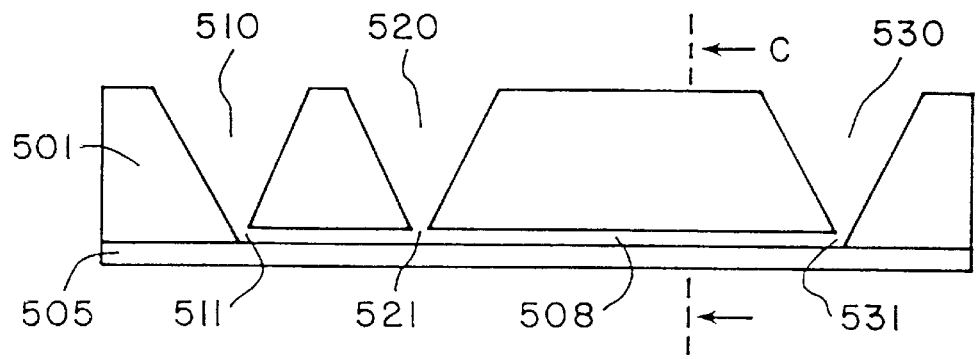
FIGS. 10A–10C, shows a sheath flow module.
Figure 10B:
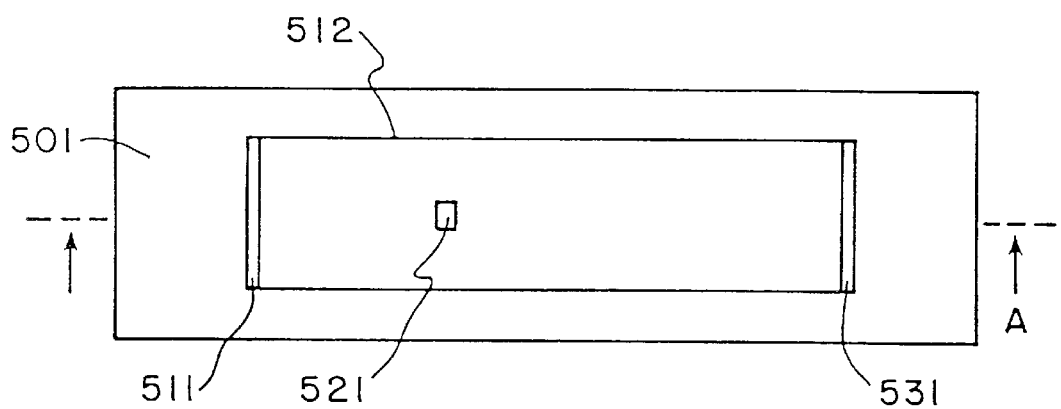
Figure 10C:
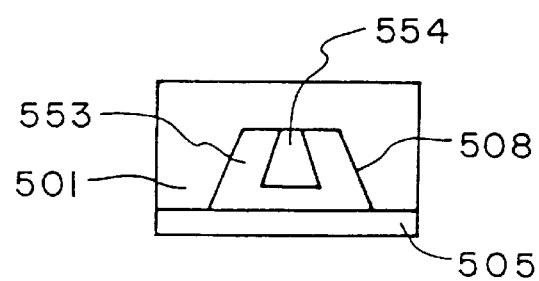

As with the v-groove channel, the order of the sheath flow module and the T-sensor can be reversed, i.e., the fluids can flow first through the sheath flow module and then through the T-sensor. FIG. 10A is a lengthwise section through the center of a flow module, as described in U.S. Patent Application "Device and Method for 3-Dimensional Alignment of Particles in Microfabricated Flow Channels," (filed Mar. 26, 1997). Plate 501 is machined, molded or etched to form the flow channel. The plate can be selected from the following which include, but are not limited to, silicon wafers, plastics, e.g., polypropylene, and casting materials. Techniques for etching silicon wafers and molding and machining plastics are well-known in the art. A laminar flow channel 508 is formed in a flat plane of the plate. A first inlet 510 passes through the plate at the upstream end of the channel and joins the flow channel at first inlet junction 511. An outlet 530 passes through the plate at the downstream end of the channel and joins the flow channel at outlet junction 531. A second inlet 520 passes through the plate between the first inlet and the outlet and joins the flow channel at second inlet junction 521, which is narrower than the first inlet junction. A second plate 505 is sealed to the flat plane of the first plate, thereby forming one side of the laminar flow channel. A view of the channel surface is illustrated in FIG. 10B. The relative widths of the inlet junctions are shown, as well as the edge 512 of the flow channel 508. The second inlet junction 521 is narrower than the first inlet junction 511. Referring again to FIGS. 10A and 10B, a sheath fluid is introduced into the flow channel 508 via the first inlet 510 and flows through the flow channel toward the outlet 530. A center fluid is introduced via the second inlet 520, preferably at lower pressure and speed than the sheath fluid. FIG. 10C is a cross section of the flow channel of FIGS. 10A and 10B, illustrating the sheath flow attained in one embodiment of the present invention. In this embodiment flow channel 508 is trapezoidal. A center fluid 554, injected from inlet 520, is surrounded on both sides (left and right) and on top by a sheath fluid 553.

Figure 11:
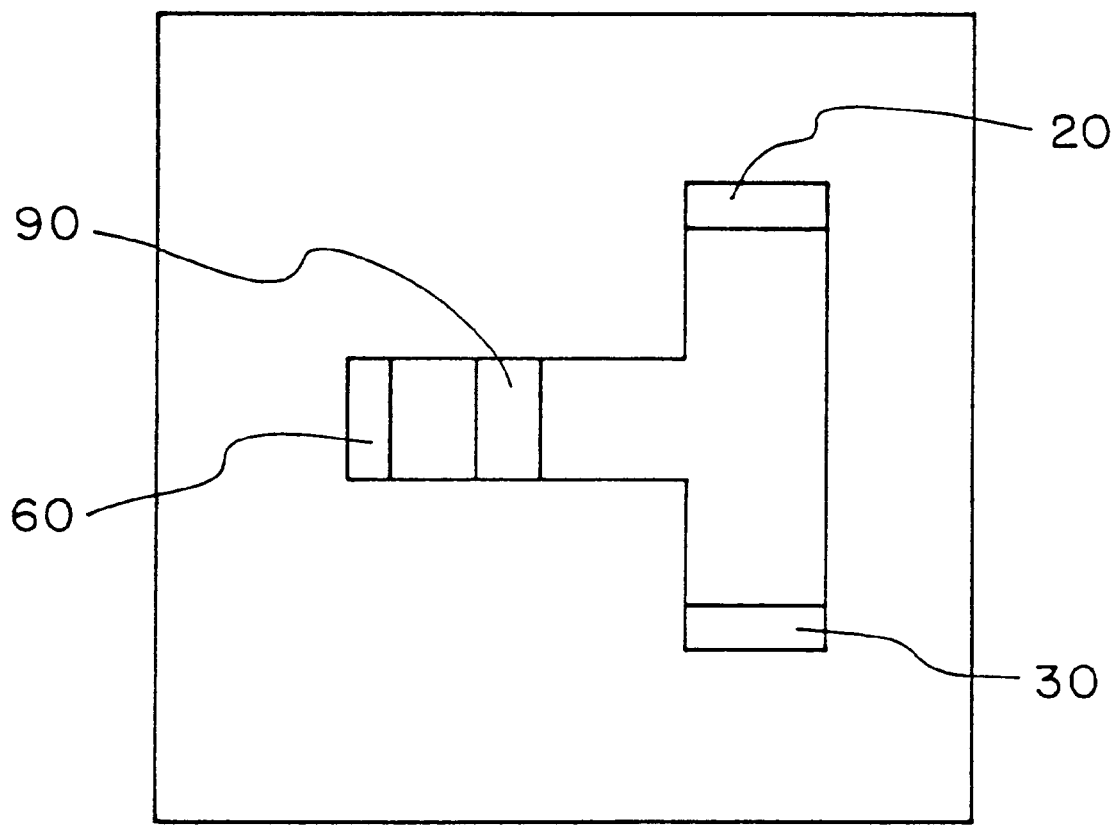
FIG. 11 shows a T-sensor in which the analyte detection area is etched all the way through the width of the substrate plate.

As discussed above, forming the channel system in a reflective material allows for optical measurements by reflection. Alternatively, optical measurements by transmission can be performed in the embodiment described next. A T-sensor channel system can be etched all the way through a substrate plate, e.g., a silicon microchip or other slab of material. The entire channel system can be etched all the way through, and therefore transect, that is, extend through the width of, the substrate plate. Alternatively, only that part of the channel system comprising the analyte detection area 90 can be etched all the way through, and therefore extend through the width of, the substrate plate, as shown in FIG. 11. Indicator stream inlet port 20, sample stream inlet port 30, and exit port 60 are shown also. An optically transparent plate, e.g., a cover plate, is sealed to both sides of the microchip. If only part of the channel system is etched all the way through the microchip, then the transparent plate need cover only that part of the microchip.

As in the other embodiments of this invention, the dimensions of the device are chosen so that laminar flow is maintained. In this embodiment, if a silicon microchip is etched by anisotropic EPW etching, it is preferable to use a thin microchip so that the channel diameters can be kept small enough to maintain laminar flow. The anisotropic EPW etching creates channels which are wider at the top than at the bottom of the channel. Etching all the way through a microchip can create a channel which is undesirably wide at the top and therefore with an undesirably large channel diameter. Undesirably large channel diameters may not maintain laminar flow. Preferable widths of a thin microchip are between 100 and 300 microns, and more preferably between 100 and 200 microns. Alternatively, other methods of etching silicon, e.g., reactive ion etching, can be used to keep channel diameters small enough to maintain laminar flow. Other materials, e.g., plastics, which are machined or molded to form the channel system need not necessarily be thin to keep channel diameters small.

A microchip can be made thinner by etching prior to formation of the channel system therein. An uncoated microchip, that is a microchip with no photoresist on it, can be made thinner by submerging it in etching solution. A channel system, or at least the analyte detection area, can then be etched all the way through the microchip.

Alternatively, a T-sensor channel system which maintains a low Reynolds number, i.e. laminar flow, can be formed wherein the depth of the channel is greater than the width. However, because the flow speed is parabolic with respect to the channel width, i.e., it is fastest in the center of the channel and approaches zero at the walls, it is preferable that the channel dimensions are such that diffusion from top to bottom and bottom to top counteracts this parabolic flow speed profile. Increasing the depth of the flow channel decreases the effect of diffusion from top to bottom and bottom to top.

Numerous embodiments besides those mentioned herein will be readily apparent to those skilled in the art and fall within the range and scope of this invention. All references cited in this specification are incorporated in their entirety by reference herein. The following examples illustrate the invention, but are in no way intended to limit the invention.

EXAMPLES

Example 1

Fabrication of Channel Cell.

A two-mask level process was used to fabricate a channel cell of this invention on a silicon wafer. The channel cell had a flow channel 400 micrometers wide and 20 mm long. The "branches" or crossbar of the "T" comprising the inlet channels was a groove 30 mm long and 200 micrometers wide. Channel depth was 50 micrometers.

The first mask level defined the inlets and outlet ports, which were etched completely through the wafer to the rear side of the silicon. The second level defined the fluid transport channels.

Four inch chrome masks were made to these specifications by Photo Sciences, Inc. (Torrance, Calif.) and 3" wafers ({100}, n-type) with 500 nm of $SiO_2$ grown on them were used.

Wafers were cleaned in a Piranha bath ($H_2SO_4$ and $H_2O_2$) (2:1) before processing. A primer (HMDS spun on at 3000 rpm) was used to enhance photoresist adhesion. About one $\mu$m of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4: 1) (Hoechst) for one minute and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylenediamine, pyro-catechol, and water (EPW F-etch as described in Reisman, A., et al. (1979) J. Electrochem. Soc. 126:1406–1415) set up in a reflux boiling flask. This etch attacks the {100} planes of silicon at a rate of about 100 $\mu m$ an hour. Fluid attachment ports were etched in the first step for about three hours. Photoresist was again applied, and the mask containing flow channels between fluid ports and the barrier region was exposed. The wafers were developed and etched in this second step for about one hour.

After final processing, the wafers were once again cleaned in a Piranha bath and rinsed in DI water. They were then diced into individual devices about 1 cm by 1 cm.

Anodic bonding according to Wallis, G. and Pomerantz, D. I. (1969) J. Appl. Physics 40:3946–3949, was used to attach Pyrex glass to the silicon devices. One inch square pieces of Pyrex glass (100 $\mu m$ thickness) from Esco Products Inc. (Oak Ridge, N.J.) were used. First, the silicon and Pyrex glass were immersed in a solution of $H_2O_2$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Example 2

Fluorescence Color changes with pH.

Five 0.01 M HEPES Buffer solutions, with pH 7.2, 7.4, 7.6, 7.8 and 8.0 were prepared from analytical grade chemicals (Aldrich). The resulting solutions were used consecutively as sample streams. The analyte in question in this experiment is $H^+$ or $OH^-$. 1 mg of the fluorescent pH indicator dye carboxy-SNAFL 2 (Molecular Probes, Eugene, OR), was dissolved in 2 ml of DMSO (((0.9%, Aldrich). 0.1 ml of this solution was mixed with 1 ml of a 0.0001M HEPES Buffer of pH 7.0. The resulting solution was used as the indicator stream.

The T-sensor channel cell was attached to the stage of a microscope so that the joint of the T-sensor was in the view field of the objective. The inlet ports and the outlet port were connected to injector loops and to upright tubes which were filled with water so that there was a pressure difference of 30 mm water column between the inlet ports and the outlet port. Both inlet ports were exposed to identical pressure so that the two streams joined in the middle of the T-joint, and were flowing parallel to the outlet port. One injector loop was filed with indicator dye solution, the other loop was filled with one of the sample solutions. The loops contained enough volume to operate the device for roughly one hour.

After both injection loops were allowed to flow into the T-sensor, and after 1 min of equilibration and flushing time, photographs were taken through a camera attachment on the microscope. The excitation filter center wavelength was 480 nm, the emission filter was a longpass 510 nm filter.

The experiment yielded photographs in which the color of the analyte detection area between the indicator stream and the sample stream was a function of the pH of the sample stream. The color changed from red over orange to yellow as the pH decreased from 8.0 to 7.2. Computer-enhanced images showed the color of the indicator stream per se to be yellow, and the analyte detection area between the streams to range from red to orange, whereas the colorless ample stream appeared black. By color mapping, numeric values are assigned to the different colors which are used to calibrate the system. Alternatively, light intensity change is measured at two wavelengths, thereby measuring the decrease of the red portion and the increase of the yellow portion of the spectrum with decreasing pH.

Example 3

Kinetic Measurements as a Function of Distance

Alkaline phosphatase in serum and 0.1M p-nitrophenol phosphate (PNPP)(weakly yellow) in 0.1M HEPES buffer, pH 7.40, were injected into a T-sensor device. The alkaline phosphatase catalyzed the reaction of PNPP to p-nitrophenol (strongly yellow) and phosphate. The formation, (and rate thereof), of p-nitrophenol was detected by an increase in yellow color. The rate of change of yellow color intensity as a function of distance from the T-joint was a function of enzyme concentration, enabling calculation of a rate constant.

We claim:

1. A channel cell system for detecting the presence of analyte particles in a sample stream also comprising larger particles comprising:
   a) a laminar flow channel;
   b) at least two inlets in fluid connection with said laminar flow channel for respectively conducting into said laminar flow channel (1) an indicator stream and (2) said sample stream;
   c) wherein said laminar flow channel has a width greater than about 20 microns, a depth sufficiently small to allow laminar flow of said streams and a length sufficient to allow particles of said analyte to diffuse into said indicator stream to the substantial exclusion of said larger particles in said sample stream to form a detection area;
   d) an outlet for conducting said streams out of said laminar flow channel to form a single mixed stream.

2. The system of claim 1 also comprising a fluorescence detector for detecting changes in an indicator substance carried within said indicator stream as a result of contact with analyte particles.

3. The system of claim 1 comprising means for conducting specimen streams from the indicator stream at successive intervals along the length of said laminar flow channel and means for measuring signals from the indicator stream in each specimen stream whereby concentration of the analyte in the sample stream may be determined.

4. The channel cell system of claim 1 wherein said indicator stream comprises reporter beads.

5. A channel cell system for detecting the presence of analyte particles in a sample stream also comprising larger particles comprising:
   a) a laminar flow channel;
   b) at least two inlet means in fluid connection with said laminar flow channel for respectively conducting into said laminar flow channel (1) an indicator stream and (2) said sample stream;

c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area; and d) a v-groove channel in fluid connection with said laminar flow channel.

6. The channel cell system of claim 5 wherein said indicator stream comprises reporter beads.

7. The channel cell system of claim 5 further comprising at least one branching flow channel in fluid connection with said laminar flow channel and said v-groove channel.

8. The channel cell system of claim 7 wherein said sample stream comprises both dissolved and undissolved particles and said dissolved particles are detected in said laminar flow channel and said undissolved particles are detected in said v-groove channel.

9. A channel cell system for detecting the presence of analyte particles in a sample stream also comprising larger particles comprising:

a) a laminar flow channel;

b) at least two inlet means in fluid connection with said laminar flow channel for respectively conducting into said laminar flow channel (1) an indicator stream and (2) said sample stream;

c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area; and d) a sheath flow module in fluid connection with said laminar flow channel.

10. The channel cell system of claim 9 wherein said indicator stream comprises reporter beads.

11. A channel cell system for detecting the presence of analyte particles in a sample stream also comprising larger particles comprising:

a) a convoluted laminar flow channel;

b) at least two inlet means in fluid connection with said laminar flow channel for respectively conducting into said laminar flow channel (1) an indicator stream and (2) said sample stream;

c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area;

d) outlet means for conducting said streams out of said laminar flow channel to form a single mixed stream.

12. The channel cell system of claim 11 wherein said convoluted laminar flow channel comprises a coiled shape.

13. The channel cell system of claim 11 wherein said convoluted laminar flow channel comprises a square wave shape.

14. The channel cell system of claim 11 further comprising a v-groove channel in fluid connection with said convoluted laminar flow channel.

15. The channel cell system of claim 11 further comprising a sheath flow module in fluid connection with said convoluted laminar flow channel.

16. A channel cell system for detecting the presence of analyte particles in a sample stream also comprising larger particles comprising:

a) a laminar flow channel;

b) at least two inlets in fluid connection with said laminar flow channel for respectively conducting into said laminar flow channel (1) an indicator stream and (2) said sample stream;

c) wherein said laminar flow channel has a width greater than about 20 microns, a depth sufficiently small to allow laminar flow of said streams and a length sufficient to allow particles of said analyte to diffuse into said indicator stream to the substantial exclusion of said larger particles in said sample stream to form a detection area;

d) an outlet for conducting said streams out of said laminar flow channel to form a single mixed stream; and e) an optical analyte detection area.

17. A method of determining a kinetic rate constant for a reaction using the channel cell system of claim 16, comprising the steps of:

(a) conducting said sample stream and said indicator stream into said laminar flow channel having an inlet;

(b) allowing analyte particles to diffuse into said indicator stream to form an analyte detection area; and (c) detecting the presence of said analyte in said indicator stream at a known distance from said inlet.

18. A channel cell system formed in a substrate plate for detecting by transmission the presence of analyte particles in a sample stream also comprising larger particles comprising:

a) a laminar flow channel;

b) at least two inlet means in fluid connection with said laminar flow channel for respectively conducting into said laminar flow channel (1) an indicator stream and (2) said sample stream;

c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area;

d) outlet means for conducting said streams out of said laminar flow channel to form a single mixed stream;

e) at least one analyte detection area between said inlet means and said outlet means;

f) optically transparent plates sealed to both sides of said substrate plate; and g) wherein said analyte detection area lies between said transparent plates in a space cut through the width of said substrate plate.

19. The channel cell system of claim 18 wherein said laminar flow channel lies between said transparent plates in a space cut through the width of said substrate plate.

* * * * *

UNITED STATES PATENT AND TRADEMARK OFFICE
CERTIFICATE OF CORRECTION

PATENT NO.    : 5,972,710

DATED         : October 26, 1999

INVENTOR(S)   : Weigl et al.

It is certified that error appears in the above-identified patent and that said Letters Patent is hereby corrected as shown below:

In column 11, line 58, please delete "The bright zone at the right is light reflecting on the silicon and does not relate to the sample and indicator streams.".

In column 11, line 60, please delete "dark" and after "right", please insert --; the fluid contains OH⁻ particles which are represented by dots.".

In column 11, line 61, please delete "bright" and replace with --dashed--.

In column 11, line 63, please delete "grey" and after "middle", please insert --represented by dashed lines and dots--.

In column 11, line 66, please delete "grey".

In column 20, line 57, please delete "x" and replace with --triangles--.

Signed and Sealed this

Twentieth Day of June, 2000

*Attest:*

Q. TODD DICKINSON

*Attesting Officer*            *Director of Patents and Trademarks*